United States Patent
Karlsson et al.

(10) Patent No.: US 10,982,016 B2
(45) Date of Patent: Apr. 20, 2021

(54) METHOD FOR MANUFACTURING A SHAPED CROSS-LINKED HYALURONIC ACID PRODUCT

(71) Applicant: Galderma Holding SA, La Tour-de-Peilz (CH)

(72) Inventors: Morgan Karlsson, Knivsta (SE); Anne Helander Kenne, Marsta (SE); Åke Öhrlund, Uppsala (SE)

(73) Assignee: GALDERMA HOLDING SA, La Tour-de-Peilz (CH)

(*) Notice: Subject to any disclaimer, the term of this patent is extended or adjusted under 35 U.S.C. 154(b) by 0 days.

(21) Appl. No.: 16/781,264

(22) Filed: Feb. 4, 2020

(65) Prior Publication Data

US 2020/0247913 A1   Aug. 6, 2020

Related U.S. Application Data

(60) Continuation of application No. 16/111,561, filed on Aug. 24, 2018, now abandoned, which is a division of application No. 14/901,546, filed as application No. PCT/EP2013/063716 on Jun. 28, 2013, now Pat. No. 10,077,321.

(51) Int. Cl.

| | | |
|---|---|---|
| *C08B 37/08* | (2006.01) | |
| *A61K 8/04* | (2006.01) | |
| *A61K 8/73* | (2006.01) | |
| *A61K 31/728* | (2006.01) | |
| *A61Q 19/00* | (2006.01) | |
| *D01F 9/00* | (2006.01) | |
| *A61Q 19/08* | (2006.01) | |
| *A61K 9/00* | (2006.01) | |

(52) U.S. Cl.
CPC .......... *C08B 37/0072* (2013.01); *A61K 8/042* (2013.01); *A61K 8/735* (2013.01); *A61K 9/0024* (2013.01); *A61K 31/728* (2013.01); *A61Q 19/00* (2013.01); *A61Q 19/08* (2013.01); *D01F 9/00* (2013.01); *A61K 2800/91* (2013.01)

(58) Field of Classification Search
None
See application file for complete search history.

(56) References Cited

U.S. PATENT DOCUMENTS

| | | |
|---|---|---|
| 2003/0094719 A1 | 5/2003 | Yang et al. |
| 2006/0046590 A1 | 3/2006 | Chu et al. |
| 2006/0105022 A1 | 5/2006 | Yokokawa et al. |
| 2007/0066816 A1 | 3/2007 | Tsai et al. |
| 2009/0263447 A1 | 10/2009 | Asius et al. |
| 2010/0210587 A1 | 8/2010 | Matsumoto |
| 2012/0034462 A1 | 2/2012 | Stroumpoulis et al. |
| 2012/0040463 A1* | 2/2012 | Domard .................... D01F 4/00 435/400 |

FOREIGN PATENT DOCUMENTS

| | | |
|---|---|---|
| EP | 0 320 164 A2 | 6/1989 |
| EP | 2 199 308 A1 | 6/2010 |
| JP | H01-197501 A | 8/1989 |
| JP | 2011-506701 A | 3/2011 |
| KR | 20070004159 A | 1/2007 |
| KR | 20080062092 A | 7/2008 |
| WO | WO-2006/051950 A1 | 5/2006 |
| WO | WO-2009/080220 A1 | 7/2009 |
| WO | WO-2010/115081 A2 | 10/2010 |
| WO | WO-2012/054311 A1 | 4/2012 |

OTHER PUBLICATIONS

Kuo, Comprehensive Biomaterials vol. 2, 2011, pp. 239-259, abstract only. (Year: 2011).*
Burdick et al., "Hyaluronic acid," Biomaterials, Artificial Organs and Tissue Engineering, 2005, [URL: https://www.sciencedirect.com/topics/chemistry/hyaluronic-acid], retrieved Jul. 31, 2019 (1 page).
Ibrahim, Acta Biomaterialia 7 (2011) 653-665.
International Preliminary Report on Patentability issued on International Application No. PCT/EP2013/063716 dated Dec. 29, 2015 (8 pages).
International Search Report issued on PCT Application No. PCT/EP2013/063716 dated Aug. 9, 2013 (5 pages).
Laurent et al., "Cross-Linked Gels of Hyaluronic Acid," Acta Chemica Scandinavica, Munksgaard, Copenhagen, DK, vol. 18, No. 1, Jan. 1, 1964, pp. 274-275.
Office Action issued on Japanese Application No. 2016-522286 dated Aug. 8, 2017 (8 pages).
Tomihata et al., "Crosslinking of Hyaluronic Acid with Water-Soluble Carbodiimide," Journal of Biomedical Materials Research, vol. 37, No. 2, Nov. 1, 1997, pp. 243-251.
Written Opinion issued on PCT Application No. PCT/EP2013/063716 dated Aug. 9, 2013 (8 pages).

* cited by examiner

*Primary Examiner* — Layla D Berry
(74) *Attorney, Agent, or Firm* — Foley & Lardner LLP; Sunit Talapatra

(57) ABSTRACT

A method for manufacturing a shaped cross-linked hyaluronic acid product including the step of subjecting a non-cross-linked precipitated hyaluronic acid substrate in a desired shape to a single cross-linking reaction in a liquid medium having a pH of 11.5 or higher and including one or more polyfunctional cross-linking agent(s) and an amount of one or more organic solvent(s) giving precipitating conditions for hyaluronic acid, under suitable conditions to obtain a precipitated, shaped cross-linked hyaluronic acid product having a degree of modification of 1-40 cross-linking agent units per 1000 disaccharide units.

25 Claims, 6 Drawing Sheets

METHOD FOR MANUFACTURING A SHAPED CROSS-LINKED HYALURONIC ACID PRODUCT

CROSS REFERENCE TO RELATED APPLICATIONS

This application is a Continuation Application of U.S. application Ser. No. 16/111,561, filed Aug. 24, 2018; which is a Divisional Application of U.S. application Ser. No. 14/901,546, filed Dec. 28, 2015 and issued as U.S. Pat. No. 10,077,321; which is a U.S. National Stage Application of PCT Application No. PCT/EP2013/063716, filed Jun. 28, 2013; which are herein incorporated by reference in their entirety.

TECHNICAL FIELD

The present invention relates to the field of polysaccharides. More specifically, the present invention is concerned with novel methods of cross-linking hyaluronic acid and of manufacturing shaped cross-linked hyaluronic acid products.

BACKGROUND

One of the most widely used biocompatible polymers for medical use is hyaluronic acid. It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical cross-linking of polymers to infinite networks. While native hyaluronic acid and certain cross-linked hyaluronic acid products absorb water until they are completely dissolved, cross-linked hyaluronic acid gels typically absorb a certain amount of water until they are saturated, i.e. they have a finite liquid retention capacity, or swelling degree.

When preparing gels from biocompatible polymers, it is advantageous to ensure a low degree of cross-linking so as to maintain a high biocompatibility. However, often a more dense gel is required to have a proper biomedical effect, and in such a case the biocompatibility will often be lost.

Since hyaluronic acid is present with identical chemical structure except for its molecular mass in most living organisms, it gives a minimum of reactions and allows for advanced medical uses. Cross-linking and/or other modifications of the hyaluronic acid molecule is necessary to improve its resistance to degradation or duration in vivo. Furthermore, such modifications affect the liquid retention capacity of the hyaluronic acid molecule. As a consequence thereof, hyaluronic acid has been the subject of many modification attempts.

Since cross-linked hyaluronic acid gel products are highly complex chemical structures, they are typically characterised by a combination of their chemical structures and their physical properties. The deviation in chemical structure from unmodified hyaluronic acid is typically reported as degree of modification, modification degree, cross-linking degree, cross-linking index or chemical modification, which all relate to the amount of cross-linking agent covalently bound to the hyaluronic acid. Throughout this text, the term degree of modification will be used. The most relevant physical properties of the cross-linked hyaluronic acid gel product are the volume of liquid that the gel can absorb and the rheological properties of the gel. Both properties describe the structural stability of the gel, often referred to as gel strength or firmness, but while the absorption of liquid can be determined for a dry gel, the rheological properties have to be measured on a gel that is swollen to a desired concentration. Traditional expressions for the liquid absorption are swelling, swelling capacity, liquid retention capacity, swelling degree, degree of swelling, maximum liquid uptake and maximum swelling. Throughout this text, the term swelling degree will be used. Regarding the rheological properties of cross-linked hyaluronic acid gel products, it can be noted that rotational rheometry is only useful for determining the rheology of liquids, whereas oscillating rheometry is necessary to determine the rheology of gels. The measurement yields the resistance of the gel to deformation in units of elastic modulus and viscous modulus. A high gel strength will give a large resistance to deformation of the gel product swollen to a desired concentration.

US 2007/0066816 discloses a process for preparing double cross-linked hyaluronic acid, involving cross-linking of a hyaluronic acid substrate in two steps with an epoxide and a carbodiimide, respectively.

EP 2 199 308 A1 discloses cross-linking of a hyaluronan powder which is dispersed in a liquid medium containing ethanol. The resulting products have a poorly controlled shape.

US 2012/0034462 A1 suggests without experimental evidence that thin strands of cross-linked HA gel can be produced by passing a solid mass of the cross-linked HA gel through a sieve or mesh.

Despite advances in the field, there remains a need for alternative methods of manufacturing shaped cross-linked hyaluronic acid products having suitable liquid retention capacity and degradation profile, but with retained biocompatibility. In particular, it is desirable to minimize the degree of modification that is needed to obtain a shaped hyaluronic acid gel product having a desired gel strength, which for instance can be measured as liquid retention capacity.

Some known soft-tissue augmentation treatments involving implants occasionally suffer from the drawback that the implant, or part thereof, migrates away from the desired site of treatment. Another problem with some known tissue augmentation treatments involving implants is that the implant is displaced from the desired site of treatment. Implant migration and displacement are disadvantageous for the patient, since they may impair the cosmetic and/or therapeutic outcome of the treatment and may impede removal of the implant, if this is desired. It is highly beneficial to maintain the integrity and location of the implant for the desired time. In order to avoid the aforementioned problems, the gel is required to have a certain gel strength in order to resist deformation. This property can be measured using rheometry in the oscillating mode.

SUMMARY

It is an object of the present invention to provide a method for manufacturing a cross-linked hyaluronic acid product having a desired shape. A specific object is to provide a method for manufacturing a cross-linked hyaluronic acid product having a shape that restricts the possibility for the product to migrate following implantation into a subject.

Another object of the present invention is to provide a method for manufacturing a shaped cross-linked hyaluronic acid product having a high biocompatibility, i.e. maintaining the high biocompatibility of the hyaluronic acid when fixed in a desirable and useful shape.

In order to achieve these underlying goals and/or other goals that are evident from the present specification, it has been realized that it is an underlying object of the present invention to provide a method for manufacturing a shaped cross-linked hyaluronic acid product having a low to moderate degree of modification while at the same time having a high gel strength as shown by low to moderate liquid retention capacity, or swelling degree.

It is a further object of the present invention to provide a method for manufacturing a shaped cross-linked hyaluronic acid product wherein the liquid retention capacity can be controlled or affected by other parameters than the degree of modification of the hyaluronic acid.

It is an object of the present invention to provide a method for manufacturing a shaped cross-linked hyaluronic acid product wherein a high proportion of the bound cross-linking agent(s) is connected in (at least) two ends, i.e. to achieve a high cross-linking efficiency.

It is a further object of the present invention to provide a shaped cross-linked hyaluronic acid product having a low to moderate degree of modification and at the same time a low to moderate liquid retention capacity, or swelling degree.

It is an object of the present invention to provide a shaped cross-linked hyaluronic acid product that has a high resistance against deformation.

For these and other objects that will be evident from this disclosure, the present invention provides according to a first aspect a method for manufacturing a shaped cross-linked hyaluronic acid product, comprising the steps of:
(i) providing a hyaluronic acid substrate dissolved in a first liquid medium, which is an aqueous solution, without any cross-linking;
(ii) precipitating the hyaluronic acid substrate by subjecting it to a second liquid medium comprising an amount of one or more first water-soluble organic solvent(s) giving precipitating conditions for hyaluronic acid without any cross-linking; wherein step (i) and/or step (ii) further comprises arranging the hyaluronic acid substrate in a desired shape; and
(iii) subjecting the non-cross-linked precipitated hyaluronic acid substrate in the desired shape to a single cross-linking step in a third liquid medium having a pH of 11.5 or higher and comprising one or more polyfunctional cross-linking agent(s) and an amount of one or more second organic solvent(s) giving precipitating conditions for hyaluronic acid, under suitable conditions to obtain a precipitated, shaped cross-linked hyaluronic acid product.

It has been found that this method advantageously allows for manufacturing of shaped cross-linked hyaluronic acid products having highly desirable properties. This method provides a good control of the cross-linking since it only occurs in solid (precipitated) phase, and not in a dissolved phase and/or between method steps. The resulting product is unique in that it is a gel with a low swelling degree despite the low degree of modification of the hyaluronic acid. It is highly surprising that a gel product having a limited swelling degree at all can be obtained with this low degree of modification. It is also surprising that a process with a single cross-linking reaction can achieve products with such desirable properties. Among many applications, this method allows for manufacturing of cross-linked hyaluronic acid products having a predefined shape that is retained during the manufacturing process. The method also allows for manufacturing of biocompatible shaped cross-linked hyaluronic acid products.

In a specific embodiment, the first two steps (i) and (ii) occur in the absence of a cross-linking agent, and the polyfunctional cross-linking agent is added in the third cross-linking step (iii). This ensures that the amount of cross-linking agent is tightly controlled, since no cross-linking agent is reacted or lost in previous steps, e.g. during the precipitation step.

In one embodiment, step (i) further comprises arranging the hyaluronic acid substrate solution in a desired shape on a hydrophobic surface; and the precipitation of the shaped hyaluronic acid substrate in step (ii) occurs on said hydrophobic surface. This is advantageous to avoid clogging of the structures and maintain their shape. The hydrophobic surface is preferably selected from fluorocarbons, polypropylene (PP), polyethylene terephthalate glycol-modified (PETG), polyethylene (PE), and polytetrafluoroethylene (PTFE)

In some embodiments, the aqueous solution of step (i) contains 40-100 vol % water and 0-60 vol % of lower alkyl alcohol(s). Thereby, an entangled structure can be achieved, which is likely to be advantageous for obtaining a gel product with desired properties.

In specific embodiments, the second liquid medium of step (ii) contains 0-30 vol % water and 70-100 vol % of the first water-soluble organic solvent(s). In some embodiments, the second liquid medium of step (ii) contains 0-10 vol % water and 90-100 vol % of the first water-soluble organic solvent(s). A high concentration of the first water-soluble organic solvent(s) is believed to be advantageous for achieving rapid precipitation. Thereby, an entangled structure can be achieved, which is likely to be advantageous for obtaining a gel product with desired properties.

In certain embodiments, the first water-soluble organic solvent(s) of step (ii) is one or more lower alkyl alcohol(s). In some embodiments, the lower alkyl alcohol is ethanol. These organic solvents provide rapid precipitation.

Step (i) and/or step (ii) further comprises arranging the hyaluronic acid substrate in a desired shape. By the terms "shaped" and "desired shape" is meant an intentional design which is useful in the final product, i.e. not just a freeze-dried or precipitated hyaluronan powder. In certain embodiments, the shape is selected from the group consisting of a particle, a fibre, a string, a strand, a net, a film, a disc and a bead, preferably having an extension of at least 0.5 mm, preferably more than 1 mm, more preferably more than 5 mm, in at least one dimension. In some embodiments, the shape of the substrate has an extension of less than 5 mm, preferably less than 1 mm, in at least one dimension. This facilitates access for the cross-linking agent(s) to a high number of the available binding sites of the precipitated hyaluronic acid products in the subsequent cross-linking step. In certain embodiments, the shape of the substrate is longitudinally extended and has a ratio between its longitudinal extension and its largest lateral extension of 5:1 or higher, such as 10:1 or higher, e.g. 20:1 or higher, and optionally 100 000:1 or lower, such as 25 000:1 or lower, e.g. 100:1 or lower. Since the longitudinally extended shape is maintained throughout the method and in the resulting product, the cross-linked product can be designed to avoid or decrease migration/displacement in vivo, but remains readily injectable. In specific embodiments, the shape is a fibre and the ratio between its length and its average diameter is 5:1 or higher, such as 10:1 or higher, e.g. 20:1 or higher, and optionally 100 000:1 or lower, such as 25 000:1 or lower, e.g. 100:1 or lower.

In certain embodiments, step (ii) involves extruding the hyaluronic acid substrate into the second liquid medium comprising an amount of the first water-soluble organic solvent(s) giving precipitating conditions for hyaluronic acid, thereby allowing the extruded hyaluronic acid substrate to form a precipitated fibre in the second liquid medium.

In some embodiments, the third liquid medium of step (iii) contains 0-35 vol % water, 65-100 vol % of the second organic solvent(s), and one or more polyfunctional cross-linking agent(s). In certain embodiments, the second organic solvent(s) of step (iii) is one or more lower alkyl alcohol(s). In some embodiments, the lower alkyl alcohol is ethanol.

In specific embodiments, the third liquid medium of step (iii) has a pH of 13 or higher. It has surprisingly been realized that performing the cross-linking on a precipitated, shaped substrate at elevated pH provides shaped gel products with efficient cross-linking, i.e. wherein a low degree of modification provides a firm gel with low swelling degree.

In specific embodiments, the polyfunctional cross-linking agent(s) is individually selected from the group consisting of divinyl sulfone, multiepoxides and diepoxides. In some embodiments, the polyfunctional cross-linking agent(s) is individually selected from the group consisting of 1,4-butanediol diglycidyl ether (BDDE), 1,2-ethanediol diglycidyl ether (EDDE) and diepoxyoctane. In certain embodiments, the polyfunctional cross-linking agent is 1,4-butanediol diglycidyl ether (BDDE).

In certain embodiments, the one or more polyfunctional cross-linking agent(s) provides a single type of cross-links. In specific embodiments, the one or more polyfunctional cross-linking agent(s) provides ether cross-links, which are stable. The present method advantageously provides single cross-linked hyaluronic acid gel products which are stable and can readily be sterilized, e.g. autoclaved.

In some embodiments, the method is further comprising the steps of:
(iv) subjecting the precipitated cross-linked hyaluronic acid product to non-precipitating conditions; and
(v) isolating the cross-linked hyaluronic acid product in non-precipitated form.

In certain embodiments, step (v) further comprises sterilizing the cross-linked hyaluronic acid product.

According to another aspect, the present invention provides a shaped cross-linked hyaluronic acid product having a degree of modification of 1-40 cross-linking agent units per 1000 disaccharide units, and a swelling degree of 4-300 mL per g hyaluronic acid. This shaped cross-linked hyaluronic acid product has highly useful properties, including a unique combination of a low to moderate degree of modification and at the same time a low to moderate swelling degree, or liquid retention capacity. Thereby, it is possible to provide a firm, cross-linked hyaluronic acid product with a desired shape, while maintaining the biocompatibility of the native hyaluronic acid. The cross-linked hyaluronic acid products according to the invention are designed in a predefined shape, or structure.

In certain embodiments, the swelling degree is 15-180 mL per g hyaluronic acid.

The modification efficiency (MoE) is a measure of the ratio between the minimum HA concentration ($C_{min}$), or rigidity/strength, of a gel and its degree of chemical modification by cross-linking agent(s). In specific embodiments, the modification efficiency is 10 or higher. In some embodiments, the modification efficiency is in the range of 20-190 or 20-150. Products with a modification efficiency of 10 or higher, such as in the range of 20-190 or 20-150, combine for the first time a low to moderate degree of modification and at the same time a low to moderate swelling degree, or liquid retention capacity. Thereby, it is possible to provide a firm, cross-linked hyaluronic acid product with a desired shape that is biocompatible and that has a high resistance to deformation.

In certain embodiments, the cross-linker ratio, which describes the proportion of total bound cross-linking agent that has bound two (or more) disaccharides, is 35% or higher. In specific embodiments, the cross-linker ratio is 40% or higher, and in some even 50% or higher. These shaped products consequently have a low number of cross-linking agents that do not provide effective cross-links in the product. The high cross-linker ratios allow for a surprisingly low total degree of modification in relation to the low to moderate swelling degree, a combination that is advantageous for biocompatibility but sufficient for maintaining the desired shape.

In some embodiments, the shaped hyaluronic acid product is cross-linked with one or more polyfunctional cross-linking agent(s) individually selected from the group consisting of divinyl sulfone, multiepoxides and diepoxides. In certain embodiments, the polyfunctional cross-linking agent(s) is individually selected from the group consisting of 1,4-butanediol diglycidyl ether (BDDE), 1,2-ethanediol diglycidyl ether (EDDE) and diepoxyoctane. In specific embodiments, the polyfunctional cross-linking agent is 1,4-butanediol diglycidyl ether (BDDE).

In certain embodiments, the shaped hyaluronic acid product is single cross-linked. A single cross-linked product has the advantage of being chemically well defined. It is advantageous that a shaped product with a single type of cross-links displays such desirable properties. In some embodiments, the shaped hyaluronic acid product is multiple cross-linked. In specific embodiments, the shaped hyaluronic acid product is cross-linked with ether cross-links. Shaped ether cross-linked hyaluronic acid gel products according to the invention are stable and can readily be sterilized, e.g. autoclaved.

In certain embodiments, the hyaluronic acid product has a shape selected from the group consisting of a particle, a fibre, a string, a strand, a net, a film, a disc and a bead. In some embodiments, the hyaluronic acid product is hollow or has several layers. In certain embodiments, the shape is longitudinally extended and has a ratio between its longitudinal extension and its largest lateral extension of 5:1 or higher, such as 10:1 or higher, e.g. 20:1 or higher, and optionally 100 000:1 or lower, such as 25 000:1 or lower, e.g. 100:1 or lower. Longitudinally extended cross-linked products can be designed to avoid or decrease migration/displacement in vivo, but remains readily injectable. In specific embodiments, the hyaluronic acid product is a fibre and the ratio between its length and its width, such as its average diameter, is 5:1 or higher, such as 10:1 or higher, e.g. 20:1 or higher, and optionally 100 000:1 or lower, such as 25 000:1 or lower, e.g. 100:1 or lower.

In some embodiments, the shaped hyaluronic acid product is present in fully swollen state. In the fully swollen state, it is preferred that the product has a longitudinally extended shape, and that its largest lateral extension is less than 5 mm, such as less than 1.5 mm, and preferably less than 0.2 mm. A longitudinally extended cross-linked product with a largest lateral extension of less than 5 mm or even lower is readily injectable. In the fully swollen state, it is furthermore preferred that the product has a longitudinally extended shape, and that its longitudinal extension is more than 2 mm, such as more than 25 mm, such as more than 500 mm. A longitudinally extended cross-linked product with a longitudinal extension of more than 2 mm or higher is advantageous because it avoids or decreases migration/displacement in vivo, In other embodiments, the shaped hyaluronic acid product is present in partially swollen or non-swollen state.

In specific embodiments, the shaped hyaluronic acid product is autoclavable. In further specific embodiments, the shaped hyaluronic acid product is autoclaved.

One of the preferred ways of manufacturing a shaped cross-linked hyaluronic acid product according to the invention is by the method according to the invention.

According to yet another aspect, the present invention provides an aqueous composition comprising a shaped cross-linked hyaluronic acid product according to the invention, and optionally a buffering agent.

In certain embodiments, the shaped hyaluronic acid product according to the invention or the aqueous composition according to the invention is useful as a medicament or medical device in a medical or surgical method.

According to a further aspect, the present invention provides the use of a shaped cross-linked hyaluronic acid product according to the invention or an aqueous composition according to the invention in cosmetic or medical surgery. Put another way, the present invention provides a shaped cross-linked hyaluronic acid product according to the invention or an aqueous composition according to the invention for use in cosmetic or medical surgery.

In some embodiments, the use is in cosmetic surgery selected from dermal filling and body contouring. In some other embodiments, the use is as a medicament in the treatment of, and/or in medical surgery selected from, dermal filling, body contouring, prevention of tissue adhesion, formation of channels, incontinence treatment, and orthopaedic applications.

According to one aspect, the present invention provides the use of a shaped cross-linked hyaluronic acid product according to the invention or an aqueous composition according to the invention in drug delivery. In alternative terms, the present invention provides a shaped cross-linked hyaluronic acid product according to the invention or an aqueous composition according to the invention for use in drug delivery.

According to yet another aspect, the present invention provides a pre-filled syringe, which is pre-filled with an sterilized, shaped cross-linked hyaluronic acid product according to the invention or an sterilized aqueous composition according to the invention.

According to one aspect, the present invention provides a method of treatment of a subject undergoing cosmetic or medical surgery, involving administration of a shaped cross-linked hyaluronic acid product according to the invention or an aqueous composition according to the invention to a subject in need thereof.

In certain embodiments, the subject is undergoing cosmetic surgery selected from dermal filling and body contouring. In certain other embodiments, the subject is undergoing medical surgery, or medical treatment, for a condition selected from dermal filling, body contouring, prevention of tissue adhesion, formation of channels, incontinence treatment, and orthopaedic applications.

DETAILED DESCRIPTION

Figure 1:
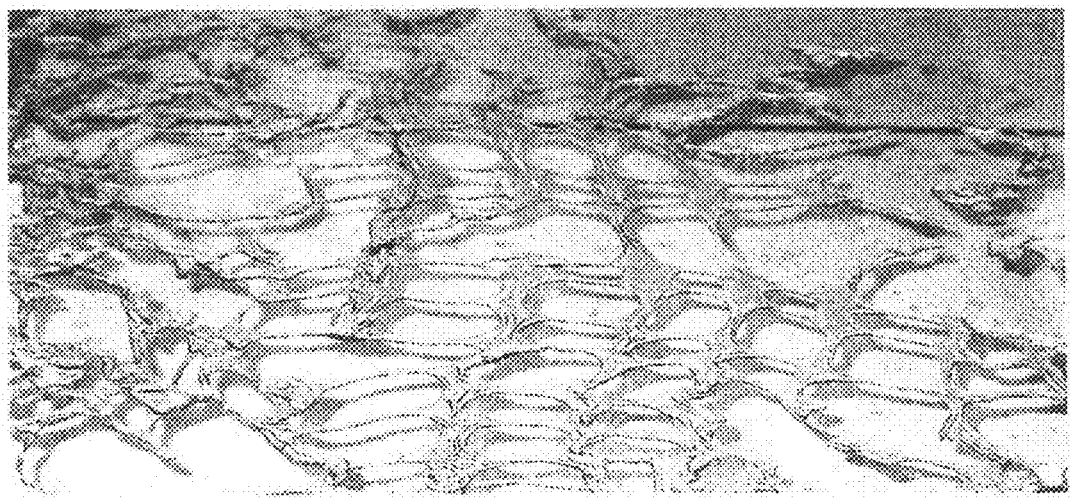
FIG. 1 shows a fully swelled cross-linked HA net.

According to one aspect, the present invention provides a manufacturing method. The method is for manufacturing a shaped cross-linked hyaluronic acid product from a hyaluronic acid substrate.

Unless otherwise provided, the term "hyaluronic acid" encompasses all variants and combinations of variants of hyaluronic acid, or hyaluronan, of various chain lengths and charge states, as well as with various chemical modifications That is, the term also encompasses the various hyaluronate salts of hyaluronic acid, such as sodium hyaluronate. Various modifications of the hyaluronic acid are also encompassed by the term, such as oxidation, e.g. oxidation of $CH_2OH$ groups to COOH; periodate oxidation of vicinal hydroxyl groups, optionally followed by reduction or imine formation, etc.; reduction, e.g. reduction of COOH to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to hyaluronic acid; and deacetylation. It is well known to the skilled person that the various forms of hyaluronic acid have different chemical properties that have to be taken into account during chemical modification and analysis. For instance, if it is desired to obtain a solution of hyaluronic acid having a certain pH, the acidity of the material to be dissolved, the acidity of the dissolving liquid and any buffering capacity will all affect the resulting pH of the solution.

It is preferred that the hyaluronic acid substrate is a hyaluronic acid or hyaluronate salt without chemical modifications, i.e. which has not been subjected to cross-linking or other modifications prior to the present manufacturing method.

The hyaluronic acid can be obtained from various sources of animal and non-animal origin. Sources of non-animal origin include yeast and preferably bacteria. The molecular weight of a single hyaluronic acid molecule is typically in the range of 1.5-3 MDa, but other ranges of molecular weights are possible, e.g. 0.5-10 MDa.

The product that is manufactured by the method is a shaped cross-linked hyaluronic acid. The method provides cross-links between the hyaluronic acid chains when they have been arranged in a desirable shape, which creates a continuous shaped network of hyaluronic acid molecules which is held together by the covalent cross-links, physical entangling of the hyaluronic acid chains and various interactions, such as hydrogen bonding, van der Waals forces and electrostatic interactions. The shaped cross-linked hyaluronic acid product according to the invention is a gel, or a hydrogel. That is, it can be regarded as a water-insoluble, but substantially dilute, cross-linked system of hyaluronic acid molecules when subjected to a liquid, typically an aqueous liquid.

The resulting shaped cross-linked hyaluronic acid product is preferably biocompatible. This implies that no, or only very mild, immune response occurs in the treated individual. In the Examples, there is provided a method of determining the biocompatibility of a hyaluronic acid product, and results from testing the biocompatibility of a cross-linked hyaluronic acid product according to the invention in rats.

The method according to the invention comprises at least three steps: a preparation step, a precipitation step, and a cross-linking step. In certain embodiments, the method is consisting of these three steps.

In the first method step, a hyaluronic acid substrate is provided. As set out above, the term "hyaluronic acid substrate" encompasses all variants and combinations of variants of hyaluronic acid, or hyaluronan, of various chain lengths and charge states, as well as with various chemical modifications. It is preferable that the hyaluronic acid substrate is a chemically unmodified hyaluronic acid or hyaluronate salt, preferably sodium hyaluronate, having an average molecular weight in the range of 0.5-10 MDa, preferably 0.8-5 MDa, more preferably 1.5-3 MDa or 2-3 MDa. It is preferred that the hyaluronic acid is obtained from non-animal origin, preferably bacteria.

The hyaluronic acid substrate is dissolved in a first liquid medium, which is an aqueous solution. By the terms "dissolved" and "solution" is understood that the hyaluronic acid substrate is present in a homogeneous mixture with a liquid, in which mixture energetically favorable interactions occur. Addition of liquid to the solution lowers the concentration of the dissolved hyaluronic acid substrate. The solution is aqueous, i.e. it contains water. The aqueous solution may simply consist of the hyaluronic acid substrate dissolved in water. It is preferable that the aqueous solution contains 40-100 vol % water and 0-60 vol % of lower alkyl alcohol(s). The term "lower alkyl alcohol" includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol and ethanol, in particular ethanol, due to price, availability and easy handling. The lower alkyl alcohol concentration is preferably in the range of 0-40%, such as 0-20%, 10-30% or 20-40% ethanol, with corresponding adjustments to the water component. The pH of this aqueous solution is suitably 6 or higher, such as 9 or higher.

Optionally, the first method step further involves arranging the hyaluronic acid substrate in a desired shape, such as a particle, a fibre, a string, a strand, a net, a film, a disc and a bead, which optionally is hollow or contain different layers of material. This may be accomplished in various ways, e.g. molding and extrusion. Extrusion of the hyaluronic acid substrate typically involves pressing the hyaluronic acid substrate solution through an opening of desired size. The extruded hyaluronic acid substrate spontaneously forms a precipitated fibre, string or strand. The dimensions, e.g. the thickness, of the fibre, string or strand can be controlled by varying the dimension or type of opening, e.g. using various opening diameters in the range of 0.1-2 mm or 14-30 G, the extrusion pressure, the extrusion speed and/or the hyaluronic acid concentration. By using other types of orifices and chinks, different shapes or structures can be produced. For instance, the hyaluronic acid can be precipitated as a film, a net, discs or beads.

In a preferred embodiment, the hyaluronic acid substrate solution is arranged in the desired shape on a hydrophobic surface, and the subsequent precipitation of the shaped hyaluronic acid substrate occurs on said hydrophobic surface. This is advantageous to avoid clogging of the shapes structures and to maintain the desired shape until it is fixed by the subsequent cross-linking step. Suitable hydrophobic surfaces are well known to the skilled person and include e.g. fluorocarbons, polypropylene (PP), polyethylene terephthalate glycol-modified (PETG), polyethylene (PE), and polytetrafluoroethylene (PTFE).

This shape can be maintained throughout the manufacturing method and in the final product. It is preferred that the shape has an extension of less than 5 mm, preferably less than 1 mm, such as less than 0.5 mm or even less than 0.2 mm, in at least one dimension when the hyaluronic acid substrate is in precipitated form. This facilitates access for the cross-linking agent(s) to a high number of available binding sites of the precipitated hyaluronic acid products in the subsequent cross-linking step. It is also preferred that the shape is longitudinally extended and has a ratio between its longitudinal extension and its largest lateral extension of 5:1 or higher, such as 10:1 or higher, e.g. 20:1 or higher, and optionally 100 000:1 or lower, such as 25 000:1 or lower, e.g. 100:1 or lower. Since the longitudinally extended shape is maintained throughout the method and in the resulting product, the cross-linked product can be designed to avoid or decrease migration/displacement in vivo, but remains readily injectable. A suitable example of such shape is a fibre and the ratio between its length and its width is 5:1 or higher, such as 10:1 or higher, e.g. 20:1 or higher, and optionally 100 000:1 or lower, such as 25 000:1 or lower, e.g. 100:1 or lower. A preferred composition is comprising cross-linked strand/fibre-shaped hyaluronic acid products according to the invention, wherein more than 50% of the products have a ratio between its longitudinal extension and its largest lateral extension of 5:1 or higher, such as 10:1 or higher, e.g. 20:1 or higher, and optionally 100 000:1 or lower, such as 25 000:1 or lower, e.g. 100:1 or lower.

By way of example, a cross-linked hyaluronic acid product according to the invention with a single strand or fibre shape filling up a 20 mL syringe may have a thickness of 1 mm and a length of 25 m in swelled state, i.e. a ratio between its longitudinal extension and its largest lateral extension of 25000:1. An example of a preferred composition comprises cross-linked strand/fibre-shaped hyaluronic acid products according to the invention, wherein more than 50% of the products have a longitudinal extension of more than 2 mm and a largest lateral extension of less than 0.2 mm, i.e. a ratio of 10:1 or higher.

The first method step is carried out without cross-linking, and this may be achieved by omitting cross-linking agents in this step and/or providing conditions that are not suitable for cross-linking. It is important to ensure that cross-linking does not occur until the preferred shape has been attained. This is advantageous for obtaining and maintaining a desired shape of the final product, since the shaping of the substrate is not limited by pre-existing cross-links, and all cross-links produced in the third step are directed to maintaining the desired shape of the product. It is preferred that the first step occurs in the absence of a cross-linking agent. This provides a good control of that the cross-linking does not occur in a dissolved phase and/or between method steps. It also ensures that the amount of cross-linking agent is tightly controlled and that the resulting products are homogenous in quality, since no cross-linking agent is reacted or lost in previous steps. Avoiding cross-linking, and in particular the addition of cross-linking agent in this step is useful to obtain a manufacturing process that is suitable for scaling up to an industrial scale and for providing products with homogenous quality.

In the second method step, the hyaluronic acid substrate is precipitated due to reduction of the solubility of the hyaluronic acid substrate. This is achieved by subjecting the hyaluronic acid substrate to a second liquid medium in which it is insoluble. The second liquid medium comprises an amount of one or more first water-soluble organic solvent(s) giving precipitating conditions for hyaluronic acid. The resulting solid precipitate falls out of the solute phase and can typically be separated from the remaining liquid by filtration, decanting, centrifugation, or manually using a pair of tweezers or the like. In one preferred embodiment, the precipitated hyaluronic acid substrate is also removed from the medium and dried. The precipitate can also be maintained suspended in the second liquid medium. Thus, in another preferred embodiment, the precipitated hyaluronic acid substrate is not subjected to drying. It is advantageous to achieve the precipitation of the hyaluronic acid substrate in a rapid fashion, e.g. by extruding or immersing the hyaluronic acid substrate in the second liquid medium in which it is insoluble.

The organic solvents that are used according to the invention are carbon-containing solvents and may exhibit a varying degree of polarity. Although termed "solvents", it shall be understood that these organic solvents are utilized for balancing and shifting the solubility of hyaluronic acid during the manufacturing method. The hyaluronic acid may very well be dissolved in an organic solvent at a certain organic solvent concentration interval, but falls out and forms a precipitate when the organic solvent concentration is increased. For instance, the hyaluronic acid can be dissolved in a 50/50 (vol/vol) mixture of an organic solvent, e.g. a lower alkyl alcohol, and water, but falls out and forms a precipitate in a 90/10 (vol/vol) mixture. When subjected to non-precipitating conditions, e.g. a 50/50 or a 0/100 mixture, the hyaluronic acid returns to the non-precipitated, dissolved state. The skilled person is well aware that other factors may have an impact on the limiting organic solvent(s) concentration for precipitation of hyaluronic acid, such as temperature, pH, ion strength and type of organic solvent(s). The limiting concentration for precipitation of hyaluronic acid under given conditions is well known or can easily be determined by a skilled person in the field. By way of example, the limiting concentration for precipitation of hyaluronic acid (in mixture of water and ethanol) is approximately 70% ethanol.

Without being limited thereto, the organic solvents according to the invention can be selected from the group consisting of pentane, hexane, cyclohexane, 1,4-dioxane, N,N-dimethylformamide, N,N-dimethylacetamide, ethyl acetate, acetamide, diethyl ether, tetrahydrofurane, acetonitrile, methyl ethyl ketone, acetone, lower alkyl alcohols, e.g. methanol, ethanol, propanol, isopropanol and butanol, It is preferable that the organic solvents according to the invention are water-soluble. A preferred group of organic solvents is the lower alkyl alcohols. The term lower alkyl alcohol includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol and ethanol, in particular ethanol, due to price, availability and easy handling.

It is suitable that the second liquid medium of the second method step is an aqueous medium, i.e. that it contains water to some extent. It is preferred that the second liquid medium contains 0-30 vol % water and 70-100 vol % of the first water-soluble organic solvent(s), preferably 0-10 vol % water and 90-100 vol % of the first water-soluble organic solvent(s). In certain embodiments, the concentration of the first water-soluble organic solvent(s) may be as high as 95%, such as 99% or even 99.5%, e.g. 99% methanol or ethanol. A high concentration of the first water-soluble organic solvent(s) is believed to be advantageous for achieving rapid precipitation. Thereby, an entangled structure can be achieved, which is likely to be advantageous for obtaining a gel product with desired properties.

The second method step is carried out without cross-linking, and this may be achieved by omitting cross-linking agents in this step and/or providing conditions that are not suitable for cross-linking. It is important to ensure that cross-linking does not occur until the preferred shape has been attained. This is advantageous for obtaining and maintaining a desired shape of the final product, since the shaping of the substrate is not limited by pre-existing cross-links, and all cross-links produced in the third step are directed to maintaining the desired shape of the product. It is preferred that the second step occurs in the absence of a cross-linking agent. This provides a good control of that the cross-linking does not occur in a dissolved phase and/or between method steps. It also ensures that the amount of cross-linking agent is tightly controlled and that the resulting products are homogenous in quality, since no cross-linking agent is reacted or lost in previous steps. Avoiding cross-linking, and in particular the addition of cross-linking agent, in this step is useful to obtain a manufacturing process that is suitable for scaling up to an industrial scale and for providing products with homogenous quality.

Optionally, the second method step further involves arranging the hyaluronic acid substrate in a desired shape, such as a particle, a fibre, a string, a strand, a net, a film, a disc and a bead, which optionally is hollow or contain different layers of material. This may be accomplished in various ways, e.g. molding and extrusion. This shape can be maintained throughout the manufacturing method and in the final product. It is preferred that the shape of the precipitated substrate has an extension of less than 5 mm, preferably less than 1 mm, such as less than 0.5 mm or even less than 0.2 mm, in at least one dimension when the hyaluronic acid substrate is in precipitated form. This facilitates access for the cross-linking agent(s) to a high number of available binding sites of the precipitated hyaluronic acid products in the subsequent cross-linking step. It is also preferred that the shape of the precipitated substrate is longitudinally extended and has a ratio between its longitudinal extension and its largest lateral extension of 5:1 or higher, such as 10:1 or higher, e.g. 20:1 or higher, and optionally 100 000:1 or lower, such as 25 000:1 or lower, e.g. 100:1 or lower. Since the longitudinally extended shape is maintained throughout the method and in the resulting product, the cross-linked product can be designed to avoid or decrease migration/displacement in vivo, but remains readily injectable. A suitable example of such shape is a fibre and the ratio between its length and its width is 5:1 or higher, such as 10:1 or higher, e.g. 20:1 or higher, and optionally 100 000:1 or lower, such as 25 000:1 or lower, e.g. 100:1 or lower. By way of example, a cross-linked hyaluronic acid product according to the invention with a single strand or fibre shape filling up a 20 mL syringe may have a thickness of 1 mm and a length of 25 m in swelled state, i.e. a ratio between its longitudinal extension and its largest lateral extension of 25000:1.

The second method step may involve extrusion of the hyaluronic acid substrate into the second liquid medium, which comprises an amount of the first water-soluble organic solvent(s) giving precipitating conditions for hyaluronic acid. This is typically involving pressing the hyaluronic acid substrate solution through an opening of desired size into the second liquid medium. The extruded hyaluronic acid substrate spontaneously forms a precipitated fibre, string or strand in the second liquid medium. The dimensions, e.g. the thickness, of the fibre, string or strand can be controlled by varying the dimension or type of opening, e.g. using various opening diameters in the range of 0.1-2 mm or 14-30 G, the extrusion pressure, the extrusion speed and/or the hyaluronic acid concentration. By using other types of orifices and chinks, different shapes or structures can be produced. For instance, the hyaluronic acid can be precipitated as a film, a net, discs or beads. When a fibre, string or strand is formed, it is preferred that the ratio between its length and its average diameter is 5:1 or higher, such as 10:1 or higher, e.g. 20:1 or higher, and optionally 100 000:1 or lower, such as 25 000:1 or lower, e.g. 100:1 or lower. An advantage with the fibre/string/strand shape is that the fibers/strings/strands themselves can be entangled at the macroscopic level, causing a coil or ball effect which may be advantageous, e.g. for maintaining the integrity of an implant.

In the third method step, the precipitated hyaluronic acid substrate is for the first time subjected to cross-linking in a third liquid medium. The term "cross-linking" refers to introduction of stable covalent links (cross-links) between (at least) two different hyaluronic acid chains or (at least) two distinct sites of a single hyaluronic acid chain, which creates a continuous network of hyaluronic acid molecules. The cross-link may simply be a covalent bond between two atoms in the hyaluronic acid chains, e.g. an ether bond between two hydroxyl groups, or an ester bond between a hydroxyl group and a carboxyl group. The cross-link may also be a linker molecule that is covalently bound to two or more atoms of different hyaluronic acid chains or distinct sites of a single hyaluronic acid chain. Although cross-linking can occur spontaneously under certain conditions, the cross-linking typically involves use of a cross-linking agent, one or more, which facilitates and speeds up the process. When the cross-linking is accomplished, the cross-linking agent(s) may be entirely or partially linked to the hyaluronic acid or it may be degraded. Any remaining residuals of non-bound cross-linking agent can be removed after the cross-linking.

It is important to ensure that cross-linking does not occur until the preferred shape has been attained. This is advantageous for obtaining and maintaining a desired shape of the final product, since the shaping of the substrate is not limited by pre-existing cross-links, and all cross-links produced in the third step are directed to maintaining the desired shape of the product. It is preferred that the first two steps occur in the absence of a cross-linking agent, and that a cross-linking agent is added in the third cross-linking step. This provides a good control of the cross-linking since it only occurs in solid (precipitated) phase, and not in a dissolved phase and/or between method steps. It also ensures that the amount of cross-linking agent is tightly controlled and that the resulting products are homogenous in quality, since no cross-linking is reacted or lost in previous steps, e.g. during the precipitation step. Altogether, focusing the cross-linking, and in particular the addition of cross-linking agent, to the final step is useful to obtain a manufacturing process that is suitable for scaling up to an industrial scale and for providing products with homogenous quality.

The third liquid medium contains one or more cross-linking agent(s) that is polyfunctional, i.e. it has two or more reaction sites for forming covalent bonds to the hyaluronic acid molecules that are being cross-linked. It is preferred that the cross-linking agent(s) that is used in this third step is bifunctional, i.e. it has two reaction sites for forming covalent bonds to the hyaluronic acid molecules that are being cross-linked. Without being limited thereto, useful polyfunctional cross-linking agents include divinyl sulfone, multiepoxides and diepoxides, such as 1,4-butanediol diglycidyl ether (BDDE), 1,2-ethanediol diglycidyl ether (EDDE) and diepoxyoctane, preferably BDDE. It is desirable that the one or more polyfunctional cross-linking agent(s) provide ether cross-links. The present method advantageously provides ether cross-linked hyaluronic acid gel products which are stable and can readily be sterilized, e.g. autoclaved. Ester cross-links are less stable and will more easily be hydrolysed.

The cross-linking of the third method step is performed under precipitating conditions so that the shaped hyaluronic acid substrate is precipitated. In particular, the available surface of the hyaluronic acid molecules is in precipitated form due to the precipitating conditions. The third liquid medium contains an amount of one or more second organic solvent(s) giving precipitating conditions for hyaluronic acid, which amount and/or organic solvent(s) may be the same as or different to what was used in the second liquid medium of the second method step to precipitate the shaped hyaluronic acid substrate.

As detailed above, it shall be understood that the organic solvents are utilized for balancing and shifting the solubility of hyaluronic acid during the manufacturing method. The skilled person is well aware that other factors may have an impact on the limiting organic solvent(s) concentration for precipitation of hyaluronic acid, such as temperature, pH, ion strength and type of organic solvent(s). The limiting concentration for precipitation of hyaluronic acid under given conditions is well known or can easily be determined by a skilled person in the field.

Using this method, it is also possible to obtain shaped cross-linked hyaluronic acid products with a single cross-linking reaction in the third method step. Depending on the choice and number of cross-linking agents in the single reaction step, the resulting shaped product may be single cross-linked, i.e. containing essentially a single type of cross-links, preferably stable ether cross-links, or multiple cross-linked, i.e. containing at least two different types of cross-links, preferably including stable ether cross-links. It is surprising that a process with a single cross-linking reaction can achieve shaped products with such desirable properties.

Without being limited thereto, the organic solvents according to the invention can be selected from the group consisting of pentane, hexane, cyclohexane, 1,4-dioxane, N,N-dimethylformamide, N,N-dimethylacetamide, ethyl acetate, acetamide, diethyl ether, tetrahydrofurane, acetonitrile, methyl ethyl ketone, acetone, lower alkyl alcohols, e.g. methanol, ethanol, propanol, isopropanol and butanol, It is preferable that the organic solvents according to the invention are water-soluble. A preferred group of organic solvents is the lower alkyl alcohols. The term lower alkyl alcohol includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol and ethanol, in particular ethanol, due to price, availability and easy handling.

It is suitable that the third liquid medium of the third method step is an aqueous medium, i.e. that it contains water to some extent. It is preferred that the third liquid medium, in addition to the cross-linking agent(s), contains 0-35 vol % water and 65-100 vol % of the second water-soluble organic solvent(s), preferably 20-35 vol % water and 65-80 vol % of the second water-soluble organic solvent(s).

The third liquid medium has a pH of 11.5 or higher, i.e. the cross-linking is performed at a pH of 11.5 or higher As the skilled person is well aware, the acidity of the hyaluronic acid starting material has to be taken into account to obtain a desired pH in the third liquid medium. This may be accomplished by addition of acids, bases or buffer systems with suitable buffering capacity. A preferred pH regulator is a strong base, such as sodium hydroxide. It has been found that a basic pH is advantageous when cross-linking the precipitated hyaluronic acid molecules. It is preferred that the third liquid medium of the third step has a pH of 13 or higher. In a liquid medium containing both water and organic solvent(s), the measured pH may differ from the theoretical pH due to the type of solvent(s) and amount of respective solvent(s). Therefore, the term apparent pH ($pH_{app}$) is introduced to indicate the pH that is measured using standard pH measurement equipment under the given conditions. An accurate pH value can readily be determined by e.g. titration.

The cross-linking in the third method step produces a shaped cross-linked hyaluronic acid product according to the invention. The shaped cross-linked hyaluronic acid product according to the invention is a gel, or a hydrogel. That is, it can be regarded as a water-insoluble, but substantially dilute cross-linked system of hyaluronic acid molecules when subjected to a liquid, typically an aqueous liquid. Since the cross-linking of the third method step is performed under precipitating conditions, both the shaped hyaluronic acid substrate and the shaped cross-linked product are precipitated. In particular, the available surface of both the shaped hyaluronic acid substrate and the shaped cross-linked product is in precipitated form due to the precipitating conditions of this third method step. The cross-linking reaction is allowed to proceed under suitable conditions until a desired amount of cross-linking agent(s) has reacted with the shaped hyaluronic acid substrate. The amount of cross-linking agent(s) that has bound to the hyaluronic acid can be quantified and reported as the degree of modification (MoD), i.e. the molar amount of bound cross-linking agent(s) relative to the total number of repeating HA disaccharide units. It is preferred that the cross-linking reaction is allowed to proceed until the degree of modification (MoD) of the cross-linked hyaluronic acid product is in the range of 1-40 cross-linking agent units per 1000 disaccharide units (0.1-4%), preferably 1-10 cross-linking agent units per 1000 disaccharide units (0.1-1%). The required reaction time is governed by several factors, such as hyaluronic acid concentration, cross-linking agent(s) concentration, temperature, pH, ion strength and type of organic solvent(s). These factors are all well known to the person skilled in the art, who easily can adjust these and other relevant factors and thereby provide suitable conditions to obtain a degree of modification in the range of 0.1-4% and verify the resulting product characteristics with respect to the degree of modification. The cross-linking of the third step occurs for at least 2 h, preferably at room temperature for at least 24 h.

Any residual non-bound cross-linking agent(s) can be removed when the shaped precipitated product is separated from the cross-linking medium. The shaped cross-linked hyaluronic acid product can be further purified by additional washing steps with a suitable washing liquid, e.g. water, methanol, ethanol, saline or mixtures and/or combinations thereof.

The manufacturing method according to the invention thus allows for a production of predefined physical forms, or structures, of the cross-linked hyaluronic acid products, such as a particle, a fibre, a string, a strand, a net, a film, a disc or a bead. Structures that are longitudinally extended, or rod-shaped, and have a ratio between their longitudinal extension and their largest lateral extension of 5:1 or higher, such as 10:1 or higher, e.g. 20:1 or higher, and optionally 100 000:1 or lower, such as 25 000:1 or lower, e.g. 100:1 or lower, are particularly useful as medical or cosmetic implants, because they can be dimensioned to avoid migration by having a sufficient length, and can at the same time readily be administered by injection through a needle due to the limited width. By way of example, a cross-linked hyaluronic acid product according to the invention with a single strand or fibre shape filling up a 20 mL syringe may have a thickness of 1 mm and a length of 25 m in swelled state, i.e. a ratio between its longitudinal extension and its largest lateral extension of 25000:1.

The predefined structures can optionally be hollow or consist of multiple layers. The space created in a hollow predefined structure is optionally filled with HA, which may be modified, such as cross-linked or substituted with other compounds. One or more of the multiple layers in a predefined layer structure may consist of cross-linked or non-cross-linked HA, which may be chemically modified by substitution with other compounds. This may be accomplished by arranging the hyaluronic acid substrate in a desired shape in the first method step, e.g. by extrusion or molding, or in the second method step, e.g. by extrusion of the dissolved hyaluronic acid substrate into a precipitating medium, e.g. ethanol. The acquired shape can be maintained throughout the manufacturing method and in the final product.

Optionally, the manufacturing method further involves a fourth step of subjecting the shaped precipitated cross-linked hyaluronic acid product to non-precipitating conditions. That is, the method is in certain embodiments comprising four steps, or alternatively consisting of four steps. This typically involves subjecting the shaped cross-linked hyaluronic acid product to a liquid medium and allowing it to return to non-precipitated state. The liquid medium is typically water, saline or mixtures and/or combinations thereof, optionally with non-precipitating concentrations of an organic solvent, e.g. methanol or ethanol. Due to the cross-linking, the resulting shaped hyaluronic acid product is a continuous network of interconnected and entangled hyaluronic acid chains which under non-precipitating conditions absorbs liquid (swells) and forms a gel. The swelling can be allowed to proceed until the gel is fully swollen and no further liquid can be absorbed, or it can be interrupted at an earlier stage to obtain a partially swollen gel. A partially swollen gel can be useful as an intermediate for further processing of the gel, for instance further mechanical production of gel structures of a desired size and shape can be performed. By way of example, a film can be cut into particles, slices or pieces, gel fibers can be cut into shorter fragments, well defined irregular shapes can be designed from a film, etc. The cross-linked HA fibers, strings or strands can also be woven together to form a net or a film after completed cross-linking, before or after drying. It may also be convenient to use a partially swollen shaped gel product during implantation thereof at a desired site to facilitate administration and minimize patient discomfort and to enhance the lifting capacity by use of the remaining swelling capacity.

When the shaped gel product is subjected to non-precipitating conditions in an excess of liquid, it is also possible to determine its maximum swelling degree, or inversely its minimum hyaluronic acid concentration ($C_{min}$), i.e. the hyaluronic acid concentration when the gel product is fully swollen. Using the manufacturing method according to the invention, it is possible to obtain a swelling degree of 4-300 mL per g hyaluronic acid, and preferably 15-180 mL per g hyaluronic acid. This implies $C_{min}$ values in the range of 0.3-25% (w/v), preferably 0.6-7% (w/v), corresponding to 3-250 mg/g, preferably 6-70 mg/g. It is highly advantageous that the desired swelling degree (or $C_{min}$ value) can be achieved with a minimal degree of modification, but the traditional way of regulating the swelling degree is by means of varying the degree of modification. The present manufacturing method therefore provides a new concept for regulating the swelling capacity of a shaped gel product, which surprisingly enables production of firm shaped gels with a uniquely high $C_{min}$ value (low swelling degree) in relation to the low degree of modification of the gel.

The modification efficiency (MoE) is a measure of the ratio between the minimum HA concentration ($C_{min}$), or rigidity/strength, of a gel and its degree of chemical modification by cross-linking agent(s). Using the manufacturing method according to the present invention, it is possible to obtain a cross-linked hyaluronic acid product having a modification efficiency of 10 or higher, preferably in the range of 10-200, such as 20-150 or 20-190. Without desiring to be limited to any specific theory, it is contemplated that the beneficial properties of the gel are the result of a surprisingly high degree of effective cross-linking, i.e. a high degree of the bound cross-linking agent(s) (cross-linker ratio, typically 0.35 or 35% or higher, such as 40% or higher or even 50% or higher) is in fact bound to the hyaluronic acid at two (or more) sites, in combination with effective positioning of the cross-links for the desired purpose, and probably an extremely high degree of retained entanglement. In contrast to what a skilled person would expect from the low degree of modification of the resulting hyaluronic acid product, the method according to the invention surprisingly provides a gel with high rigidity/strength. Under any circumstances, the method according to the invention provides a useful way of further regulating the swelling degree in relation to the degree of modification. The method is also very suitable for continuous operation, which is advantageous for large-scale production.

Optionally, the manufacturing method also involves a final step of isolating the cross-linked hyaluronic acid product. That is, the method is in certain embodiments comprising four or five steps, or alternatively consisting of four or five steps. Depending on whether the product is held under precipitating conditions or has been subjected to non-precipitating conditions, this step may involve isolating the product in precipitated form or in non-precipitated form. The isolated, precipitated or non-precipitated, product can then be subjected to sterilization so as to obtain a sterile cross-linked hyaluronic acid product.

If desired, other substances, such as local anesthetics (e.g. lidocaine hydrochloride) anti-inflammatory drugs, antibiotics and other suitable supportive medications, e.g. bone growth factors or cells, may be added after the cross-linked hyaluronic acid product has been obtained.

According to one aspect, the invention provides a shaped cross-linked hyaluronic acid product. According to one embodiment, the product is manufactured, or can be manufactured, by the manufacturing method of the invention. The shaped cross-linked hyaluronic acid product according to the invention is a gel, or a hydrogel. That is, it can be regarded as a water-insoluble, but substantially dilute cross-linked system of hyaluronic acid molecules when subjected to a liquid, typically an aqueous liquid. The gel is mostly liquid by weight and can e.g. contain 90-99.9% water, but it behaves like a solid due to a three-dimensional cross-linked hyaluronic acid network within the liquid. Due to its significant liquid content, the shaped gel is structurally flexible and similar to natural tissue, which makes it very useful as a scaffold in tissue engineering and for tissue augmentation. It is the cross-links and their attachment positions at the hyaluronic acid molecules that, together with the natural entanglement of the hyaluronic acid chains, give the gel its structure and properties, which are intimately related to its swelling degree.

The amount of attached cross-linking agent(s) can be quantified by and reported as the degree of modification (MoD), i.e. the molar amount of bound cross-linking agent(s) relative to the total number of repeating HA disaccharide units. It is preferred that the cross-linked hyaluronic acid product according to the invention has a degree of modification of 1-40 cross-linking agent units per 1000 disaccharide units (0.1-4%), preferably 1-10 cross-linking agent units per 1000 disaccharide units (0.1-1%). The effectiveness of the cross-linking reaction is shown by the amount of attached cross-linking agent(s) that is connected in (at least) two ends to one (or more) hyaluronic acid chains and is reported as the cross-linker ratio (CrR). It is preferable that the product according to the invention has a cross-linker ratio of 35% or higher, preferably 40% or higher, more preferably 50% or higher, such as in the ranges of 35-80%, 40-80% and 50-80%. These products consequently have a low number of cross-linking agents that do not provide effective cross-links in the product. The high cross-linker ratios allow for a surprisingly low total degree of modification in relation to the gel strength, which in turn is advantageous to ensure high biocompatibility.

Another characteristic of a gel is its capacity to absorb water until it is fully swollen. Further addition of liquid will not dilute the gel further, i.e. the gel cannot be indefinitely diluted like a solution of free molecules. When the gel is subjected to non-precipitating conditions, it is also possible to determine its swelling degree, or inversely its minimum concentration ($C_{min}$), i.e. the hyaluronic acid concentration when the gel product is fully swollen. Harder (low-swelling) gels are generally less viscous, more elastic and expected to have a longer half-life in vivo than softer (high-swelling) gels. However, harder gels may be recognized as foreign materials by the body if they are highly chemically modified. It is preferred that the product according to the invention has a swelling degree of 4-300 mL per g hyaluronic acid, and preferably 15-180 mL per g hyaluronic acid. This implies $C_{min}$ values in the range of 0.3-25% (w/w), i.e. 3-250 mg/g, such as 0.6-7% (w/w), i.e. 6-70 mg/g. It is preferred that the $C_{min}$ value is 0.6-5% (w/v), i.e. 6-50 mg/mL.

It is preferred that the shaped cross-linked hyaluronic acid product according to the inventions is cross-linked with one or more cross-linking agent(s) that is polyfunctional, i.e. it has two or more reaction sites for forming covalent bonds to the hyaluronic acid molecules that are being cross-linked. It is preferred that the cross-linking agent(s) is bifunctional, i.e. it has two reaction sites for forming covalent bonds to the hyaluronic acid molecules that are being cross-linked. Without being limited thereto, useful polyfunctional cross-linking agents include divinyl sulfone, multiepoxides and diepoxides, such as 1,4-butanediol diglycidyl ether (BDDE), 1,2-ethanediol diglycidyl ether (EDDE) and diepoxyoctane, preferably BDDE. It is desirable that the hyaluronic acid gel product is cross-linked with ether cross-links, which are stable.

The shaped hyaluronic acid gel product can be multiple cross-linked, i.e. containing at least two different types of bonds, preferably including ether bonds. It is preferred that the hyaluronic acid product is single cross-linked, i.e. containing essentially a single type of cross-links, preferably ether cross-links. A single cross-linked product has the advantage of being chemically well defined. It is advantageous that a product with a single type of cross-links displays such desirable properties. In specific embodiments, the hyaluronic acid product is cross-linked with ether cross-links, which provides a stable and autoclavable product.

It is highly advantageous that the desired swelling degree (or value) of the shaped product is obtained with a minimal degree of modification, although the traditional way of regulating the swelling degree is by means of varying the degree of modification. The main reason for minimizing the degree of modification is to ensure that the biocompatibility of the gel is high, but the skilled person is well aware of other advantages. The shaped product is characterised by a uniquely high $C_{min}$ value (low swelling degree) in relation to the degree of modification of the gel. The modification efficiency (MoE) is a measure of the ratio between the minimum HA concentration ($C_{min}$), that reflects the rigidity and the strength of a gel, and the degree of chemical modification of the gel with cross-linking agent(s). The shaped cross-linked hyaluronic acid product according to the invention has a modification efficiency of 10 or higher, preferably in the range of 10-200, such as in the range of 20-150 or 20-190. Products with a modification efficiency of 10 or higher, such as in the range of 20-190, combine for the first time a low to moderate degree of modification and at the same time a low to moderate swelling degree, or liquid retention capacity. Thereby, it is possible to provide a firm, cross-linked hyaluronic acid product that is biocompatible and that has a high resistance to deformation.

Furthermore, it is preferable that the shaped cross-linked hyaluronic acid gel products according to the invention are viscoelastic. This implies that the gel products exhibit a combination of viscous and elastic properties. As is well known by the skilled person, the viscoelastic properties can be determined with a rheometer. In oscillating mode, the elastic modulus (G') and the viscous modulus (G") can be determined at a frequency of 0.1 or 1 Hz. For certain viscoelastic gel products according to the invention, it is preferred that the following relationship is satisfied:

$$0.1 \le \frac{G'}{(G'' + G')} \le 0.98, \text{ preferably } 0.5 \le \frac{G'}{(G'' + G')} \le 0.98.$$

The product according to the invention is manufactured in predefined physical forms, or structures, such as a particle, a fibre, a string, a strand, a net, a film, a disc or a bead, which optionally is hollow or consists of different layers of hyaluronic acid materials. Structures that are longitudinally extended, or rod-shaped, and have a ratio between their longitudinal extension and their largest lateral extension of 5:1 or higher, such as 10:1 or higher, e.g. 20:1 or higher, and optionally 100 000:1 or lower, such as 25 000:1 or lower, e.g. 100:1 or lower, are particularly useful as medical or cosmetic implants, because they can be dimensioned to avoid migration by having a sufficient length, and can at the same time readily be administered by injection through a needle due to the limited width. When a fibre, string or strand is formed, it is preferred that the ratio between its length and its width or its average diameter, is 5:1 or higher, such as 10:1 or higher, e.g. 20:1 or higher, and optionally 100 000:1 or lower, such as 25 000:1 or lower, e.g. 100:1 or lower. By way of example, a cross-linked hyaluronic acid product according to the invention with a single strand or fibre shape filling up a 20 mL syringe may have a thickness of 1 mm and a length of 25 m in swelled state, i.e. a ratio between its longitudinal extension and its largest lateral extension of 25000:1. A preferred string thickness interval is 50-200 μm.

The gel products may be designed as hollow containers that contain human cells, drugs or other substances. According to one embodiment of the invention, a cross-linked HA gel product may be useful as a drug delivery device and be used in a method of drug delivery. According to an embodiment of the invention, a cross-linked HA gel product may be combined with non-cross-linked HA or cross-linked HA with a different degree of modification or degree of cross-linking. For instance, the cross-linked gel product may be produced in a desired container shape. The container may form a reservoir for non-cross-linked HA or cross-linked HA with a different, e.g. lower, degree of modification, which can then be slowly released or kept contained for the purpose of modulating the total strength of the resulting combination product.

Due to the cross-linking, the shaped hyaluronic acid product is a continuous network of interconnected and entangled hyaluronic acid chains which under non-precipitating conditions absorbs liquid (swells) and forms a gel. The swelling can be allowed to proceed until the gel is fully swollen and no further liquid can be absorbed. Thus, the shaped cross-linked hyaluronic acid product may be provided in fully swollen state. The swelling can also be interrupted at an earlier stage to obtain a partially swollen gel. A partially swollen gel can be useful as an intermediate for further processing of the gel, for instance production of gel structures or pieces of a desired size and shape. It may also be convenient to use a partially swollen gel during implantation thereof at a desired site to facilitate administration and minimize patient discomfort. The shaped cross-linked hyaluronic acid product according to the invention can therefore also be provided in partially swollen or non-swollen state.

The shaped cross-linked hyaluronic acid product according to the invention is useful in cosmetic or medical surgery. Non-limiting examples of cosmetic surgery are dermal filling and body contouring. Non-limiting examples of medical surgery are dermal filling, body contouring, prevention of tissue adhesion, orthopaedic applications, incontinence treatment, treatment of vesicoureteral reflux (VUR), and formation of channels for draining purposes, e.g. in ophthalmology, and for keeping tissues apart. The shaped cross-linked hyaluronic acid product according to the invention is also useful in drug delivery. It can furthermore be used as a film for post-surgical (interperitorial) adhesion and in hip and joint therapy.

According to one aspect, the present invention provides a method of treatment of a subject undergoing cosmetic or medical surgery, involving administration of a shaped cross-linked hyaluronic acid product according to the invention to a subject in need thereof. Non-limiting examples of medical surgery are dermal filling, body contouring, prevention of tissue adhesion, orthopaedic applications, e.g. hip and joint therapy, and formation of channels for draining purposes, e.g. in ophthalmology, and for keeping tissues apart.

According to one embodiment of the invention, the shaped cross-linked hyaluronic acid gel product can be brought into further structures or pieces with different shapes having a size, when subjected to a physiological salt solution, above 0.1 mm. It is preferred that cross-linked hyaluronic acid products according to the invention have a longitudinally extended shape, and that the largest lateral extension is less than 5 mm, preferably less than 1.5 mm, such as less than 0.8 mm or even less than 0.5 mm in fully swollen state. This is advantageous for the purpose of injecting the swollen gel products through a syringe of desired dimensions. It is also preferred that shaped cross-linked hyaluronic acid products according to the invention have a longitudinally extended shape, and that the longitudinal extension is more than 5 mm, preferably more than 500 mm (0.5 m), such as more than 5 m or even more than 25 m in fully swollen state. Among many possibilities, this longitudinal extension prevents migration and/or displacement of an implanted gel product in vivo.

The desired shape and size is arranged during the manufacturing of the product, i.e. by arranging the substrate in a desired shape prior to cross-linking. Another suitable way of obtaining a desired structure size involves manufacturing a shaped cross-linked hyaluronic acid gel at a desired concentration and subjecting the gel to mechanical disruption, such as mincing, mashing or passing the swollen or partly swollen gel, or the precipitated cross-linked product, through a filter or mesh with suitable pore size. The resulting gel particles or pieces are dispersed in a physiological salt solution, resulting in a gel dispersion or slurry with particles of desired size and shape. Depending on the shape, the size of a gel structure may be determined in any suitable way, such as by laser diffraction, microscopy, filtration, etc., and is decided by the longest distance between two ends of the particle. For spherical structures, the diameter equals the size for this purpose.

Useful gel structure size ranges and shapes depend on the intended application. For soft tissue augmentation, preferably subcutaneous administration, submuscular administration or supraperiostal administration, gel particles, pieces or fibers having a size, when subjected to a physiological salt solution, of more than 0.1 mm are useful. The term "soft tissue augmentation", as used herein, refers to any type of volume augmentation of soft tissues, including, but not limited to, facial contouring (e.g. more pronounced cheeks or chin), correction of concave deformities (e.g. post-traumatic, HIV associated lipoatrophy) and correction of deep age-related facial folds. Thus, soft tissue augmentation may be used solely for cosmetic purposes or for medical purposes, such as following trauma or degenerative disease. These two purposes are easily distinguished by the skilled person. The term "soft tissue", as used herein, refers to tissues that connect, support, or surround other structures and organs of the body. Soft tissue includes muscles, fibrous tissues and fat. Soft tissue augmentation may be performed in any mammal, including man. It is preferred that the method is performed in a human subject.

The terms "subepidermal administration" or "subcuticular administration", as used herein, refer to administration beneath the epidermis of the skin, including administration into the dermis, subcutis or deeper, such as submuscularly or into the periosteum where applicable (in the vicinity of bone tissue).

Administration of gel structures may be performed in any suitable way, such as via injection from standard cannulae and needles of appropriate sizes or surgical insertion, e.g. in the case of administration of a film. The administration is performed where the soft tissue augmentation is desired, such as the chin, cheeks or elsewhere in the face or body.

An implant according to the invention may be an aqueous composition comprising the shaped cross-linked hyaluronic acid product according to the invention, e.g. in the shape of ≥0.1 mm large hyaluronic acid gel structures, such as particles, beads, fibers or cut-out stripes, and optionally a buffering agent. The composition may typically contain a physiological salt buffer. The composition may further comprise other suitable additives, such as local anesthetics (e.g. lidocaine hydrochloride), anti-inflammatory drugs, antibiotics and other suitable supportive medications, e.g. bone growth factors or cells. The shaped cross-linked hyaluronic acid product according to the invention, or an aqueous composition thereof, may be provided in a pre-filled syringe, i.e. a syringe that is pre-filled with a sterilized, shaped cross-linked hyaluronic acid product or a sterilized aqueous composition comprising the shaped product. Optionally, the shaped cross-linked hyaluronic acid product may be kept in precipitated form in a syringe, bag or other suitable container and be brought to its non-precipitated form prior to injection or in the body following injection thereof.

It is preferred that the swelled or partly swelled, shaped cross-linked hyaluronic acid product is autoclavable, since this is the most convenient way of sterilizing the final product. This allows for preparation of a sterile, shaped cross-linked hyaluronic acid product.

It goes without saying that the size of the gel structures, e.g. fibers, according to the invention is dependent upon how much the gel has been allowed to swell, and the ionic strength of the buffer, solution or carrier that is included in and/or surrounding the gel structures. Throughout this specification, given structure sizes assume physiological conditions, particularly isotonic conditions. It shall be noted that, while it is preferred that the gel structures contain and are dispersed in a physiological salt solution, it is contemplated that the gel structures according to the invention can temporarily be brought to different sizes by subjecting the gel structures to a solution of another tonicity, different pH or if the gel structures have not been allowed to swell to their maximum size.

As used herein, a physiological, or isotonic, solution is a solution having an osmolarity in the range of 200-400 mOsm/l, preferably 250-350 mOsm/l, more preferably approximately 300 mOsm/l. For practical purposes, this osmolarity is easily achieved by preparation of a 0.9% (0.154 M) NaCl solution.

The shaped cross-linked hyaluronic acid gel product according to the invention is stable, but not permanent, under physiological conditions. The stability in vitro is demonstrated in Example 7 by an accelerated stability study at 60° C. for 14 days. According to an embodiment of the invention, at least 70%, preferably at least 90%, of the shaped cross-linked hyaluronic acid gel product remains for at least two weeks in vivo, more preferably between two weeks and two years. The term "degraded" implies that less than 20%, preferably less than 10%, of the medium remains in the body.

The shaped cross-linked hyaluronic acid gel product according to the invention is more resistant to biodegradation in vivo than natural hyaluronic acid. The prolonged presence of the stable gel product is advantageous for the patient, since the time between treatments is increased. It is also important that the product is highly similar to native hyaluronic acid, in order to maintain the high biocompatibility of the native hyaluronic acid. A product that is similar to native HA should be degradable by the enzyme hyaluronidase, preferably to a degree of at least 99%. The biodegradability of the firm hyaluronic acid gel products according to the invention are demonstrated in Example 8, where they are recognized by hyaluronidase. This reflects their similarity to native hyaluronic acid.

Definitions

Throughout this disclosure, the terms below are defined as follows.

| Term | Property | Meaning |
|---|---|---|
| HA | | HA refers to sodium hyaluronate |
| Gel-form HA | | Gel-form HA is the cross-linked HA that cannot be extracted from the gel by rinsing with e.g. saline, as opposed to the extractable HA |
| Extractable HA | | Extractable HA is the HA, cross-linked or not cross-linked, that can be extracted by rinsing with e.g. saline |
| $C_{HA}$ | HA concentration | $C_{HA} = \dfrac{m_{HA}}{m_{sample}}$ or $C_{HA} = \dfrac{m_{HA}}{V_{sample}}$ <br><br> Expressed in mg/g, mg/mL, % (w/w), % (w/v) |
| SwD | Swelling Degree | $SwD = \dfrac{m_{fully\ swollen\ gel}}{m_{gel\text{-}form\ HA\ in\ fully\ swollen\ gel}}$ <br><br> SwD is preferably expressed in g/g, mL/g, or as a dimensionless number. SwD is the inverted concentration of gel-form HA in a gel that is fully swollen in 0.9% saline, i.e. the volume, or mass, of fully swollen gel that can be formed per gram dry cross-linked HA. SwD describes the maximum liquid-absorbing (0.9% saline) capability of the product. |
| $C_{min}$ | Minimum HA Concentration | Concentration of gel-form HA in a gel that is fully swollen in 0.9% saline, normally expressed in mg/g or mg/mL. <br> $C_{min}^{-1}$ = SwD |
| GelC | Gel Content | $GelC = \dfrac{m_{HA\ in\ gel\text{-}form}}{m_{HA\ total}}$ <br><br> Expressed as g/g, a dimensionless number, or %. The Gel Content is the proportion of HA that is bound in gel-form out of the total HA content in the product. |
| MoD | Degree of Modification | $MoD = \dfrac{n_{bound\ crosslinking\ agent}}{n_{disaccharide\ units}}$ <br><br> Expressed as mole/mole, a dimensionless number, or mole %. MoD describes the amount of cross-linking agent(s) that is bound to HA, i.e. molar amount of bound cross-linking agent(s) relative to the total molar amount of repeating HA disaccharide units. MoD reflects to what degree the HA has been chemically modified by cross-linking agent(s). |
| CrR | Cross-linker ratio | $CrR = \dfrac{n_{HA-X-HA}}{n_{HA-X-HA} + n_{HA-X}}$ <br><br> where X is a cross-linking agent. CrR can also be expressed as: <br><br> $CrR = \dfrac{\#crosslinked\ crosslinking\ agents}{\#bound\ crosslinking\ agents}$ |

| Term | Property | Meaning |
|---|---|---|
| | | Expressed in mole/mole, a dimensionless number, or mole %. CrR describes the proportion of total bound cross-linking agent (HA-X-HA and HA-X) that has bound two (or more) disaccharides (only HA-X-HA). |
| MoE | Modification Efficiency | $MoE = \dfrac{C_{min}}{MoD}$<br><br>MoE is a dimensionless number obtained as the ratio between $C_{min}$ expressed in mg/g and MoD expressed in %. MoE describes the amount of interconnections, caused both by chemical modification and from molecular entanglements, which have been achieved at the cost of a certain degree of chemical modification by cross-linking agent(s).<br>Example: MoE for a product with $C_{min}$ = 35 mg/mL and MoD = 1.15% is approximately 30, and is calculated as follows:<br><br>$MoE = \dfrac{35}{1.15} \approx 30$ |
| G' | Elastic modulus | The elastic modulus describes the resistance of the gel to elastic deformation, and is expressed in Pa (Pascal). A strong gel will give a larger number compared to a weak gel. |
| G" | Viscous modulus | The viscous modulus describes the resistance of the gel to viscous deformation, and is expressed in Pa (Pascal). Together with G', it describes the total resistance to deformation. |

Without desiring to be limited thereto, the present invention will in the following be illustrated by way of examples.

EXAMPLES SECTION

Analytical Methods
Determination of HA Concentration

The method for determination of HA content is adopted from the assay test for sodium hyaluronate described in Ph. Eur. 1472. The principle for the method is that a condensation reaction of the furfural derivatives formed by heating in sulphuric acid occurs with the carbazole reagent, forming a purpur colored product. The reaction is specific for the D-glucuronic acid part of HA. The absorbance is measured at 530 nm and glucuronic acid is used for standardization.

The product formed from the content of D-glucuronic acid (GlcA) in the sample is determined by reaction with carbazole. To get homogeneous sample solutions, the stabilized gel of HA is degraded with sulphuric acid at 70° C. and diluted with 0.9% NaCl-solution. The solutions are mixed with sulphuric acid at 95° C. and thereafter with carbazole reagent. The reactions result in pink colored solutions. The intensity of the color is measured with a colorimeter at 530 nm, and the absorbance of each sample is directly proportional to the GlcA-content. The HA content is calculated from the GlcA-content in each sample.

Determination of Gel Content (GelC)

GelC describes in % the proportion of the total HA that is bound in gel form. Gel content is defined as the amount of HA in a sample that does not pass through a 0.22 μm filter. GelC is calculated from the amount of HA that is collected in the filtrate, here denoted extractable HA. The gel content and the extractable HA content are given in percent of the total amount of HA in the gel sample. In short, the gel content is determined by mixing a certain amount of gel sample with 0.9% NaCl in a test tube. The gel is allowed to swell where after the NaCl-phase is separated from the gel-phase by filtration through a 0.22 μm filter. The concentration of HA in the filtrate is determined according to the procedure for determination of HA concentration.

Determination of Swelling Degree (SwD)

SwD describes the liquid-absorbing capability of a product, i.e. its capability to absorb 0.9% NaCl. The product is typically a dry, cross-linked HA gel. The dry product may be precipitated or not precipitated. SwD can be determined from the weight of fully swollen product that is formed upon swelling a certain weight of a dry product in saline. If the dry product is precipitated, it will revert to non-precipitated form under these conditions.

Dry product with a predetermined weight (typically 0.1 g) is subjected to an excess of 0.9% NaCl(aq), and the product is allowed to swell for one hour at room temperature (23° C.). The fully swollen products are collected and weighed after removing non-absorbed liquid. Removal of non-absorbed liquid also removes any substances that are not bound to or entangled in the cross-linked gel, such as non-cross-linked and weakly cross-linked hyaluronate molecules. Since these which will not contribute to the weight of the fully swollen product, thereby giving an apparently lower SwD, correction for the gel content should be made in order to determine the true SwD. If the gel content is considered close enough to 100% that the result is not affected, this correction may be omitted.

SwD is calculated as the ratio between weight of product, fully swollen and rinsed from extractable HA as described above, and weight of the dry cross-linked HA in the product:

$$SwD = \frac{m_{fully\ swollen\ gel}}{m_{gel-form\ HA\ in\ fully\ swollen\ gel}} = \frac{m_{fully\ swollen\ gel}}{m_{dry} \times GelC},$$

wherein GelC is expressed as a dimensionless number. If GelC is considered close to 1 (100%), SwD can be calculated as:

$$SwD = \frac{m_{fully\ swollen\ gel}}{m_{dry}}$$

Three techniques of collecting the fully swollen product and removing non-absorbed liquid have been used: 1) collecting the swollen product piece by piece, allowing the products to briefly touch a dry surface, 2) collecting all of the swollen product using a metal net, allowing the net to briefly touch a dry surface, 3) removing liquid from the swollen product by suction through a 0.2 μm filter. In the latter case, the weight of the fully swollen product was not weighed directly, but calculated from the weight of the dry sample before swelling, the weight of the added liquid and the weight of the liquid removed upon filtration, using the formula:

$$m_{fully\ swollen\ gel\ product} = m_{added\ liquid} - m_{removed\ liquid} + m_{dry\ product}$$

Notably, a stronger gel will have a lower SwD, while a weaker gel will have a higher SwD.

Determination of Minimum Concentration ($C_{min}$)

$C_{min}$ describes the concentration of gel-form HA in a cross-linked HA gel product, fully swollen in 0.9% NaCl after all extractable HA is removed. Since the product cannot absorb more liquid, this concentration is the minimum HA concentration that can be obtained for this particular gel product. Notably, a stronger gel will have a higher $C_{min}$, while a weaker gel will have a lower $C_{min}$.

The $C_{min}$ is determined in analogy with the determination of SwD as set out above, using the relation:

$$C_{min} = \frac{1}{SwD}.$$

Determination of Degree of Modification (MoD)

MoD describes the molar amount of bound cross-linking agent(s) relative to the total number of repeating HA disaccharide units. This measure does not distinguish between mono-linked and actually cross-linked cross-linking agent(s), i.e. all cross-linking agent(s) that is bound to HA via at least one covalent bond is included. For instance, a MoD of 1% for a HA gel cross-linked with BDDE means that there is 1 bound (monolinked or cross-linked) molecule of BDDE per 100 disaccharide units in the HA gel.

MoD is determined using NMR spectroscopy on enzymatically degraded gel product. Soluble HA, residual (non-bound) cross-linking agent(s) and derivatives thereof are washed away prior to the degradation of the gel by filtration on a 0.22 μm filter. The gel product is degraded at 37° C. by enzymatic treatment using Chondroitinase AC from *Arthrobacter aurescens*. The degraded gel product is subjected to NMR spectroscopy by recording one-dimensional $^1$H NMR spectra on a 400 MHz spectrometer, equipped with a standard 5 mm probe.

The NMR spectra are evaluated by integration of the signal at $\delta_H$ 1.6 ppm, which origins from four protons in the linked BDDE molecule, and the signals at OH 2.0 ppm, which is from the three protons in the $CH_3$ groups on the N-acetylglucosamine residues of the HA disaccharides. The ratio between the integrals for these two signals is proportional to the ratio between the molar amount of bound BDDE and disaccharides after correction for the number of protons responsible for each signal, hence giving MoD.

$$MoD = \frac{n_{bound\ crosslinking\ agent}}{n_{disaccharide\ units}}$$

Determination of Modification Efficiency (MoE)

MoE is the ratio between the minimum HA concentration and the degree of modification of a gel, i.e.:

$$MoE = \frac{C_{min}}{MoD} = \frac{1}{SwD \times MoD}$$

$C_{min}$ (mg/g or mg/mL) and MoD (%) are determined as described previously. Since $C_{min}$ is closely related to the strength of a gel, MoE is a measure of how efficient the cross-linking procedure is in producing a gel of desired strength. A process with a high MoE will produce a gel with a high $C_{min}$ and a low MoD, i.e. a strong gel is produced despite limited chemical modification of the HA.

Determination of Cross-Linker Ratio (CrR) CrR describes the proportion of total bound cross-linking agent(s) (HA-X-HA and HA-X) that has bound two (or more) disaccharides (only HA-X-HA):

$$CrR = \frac{n_{HA-X-HA}}{n_{HA-X-HA} + n_{HA-X}}$$

where X is a cross-linking agent.

The method is based on determination of HA-X fragments using SEC-UV-MS following degradation of the HA gel using chondroitinase AC from *Arthrobacter aurescens* or chondroitinase ABC from *Proteus vulgaris* into fragments consisting of the main disaccharide (Δdi-HA) and fragments with bound cross-linking agent (HA-X) containing 1-16 disaccharides. The fragments are separated using size exclusion chromatography (SEC), and detected using mass spectrometry (MS). The peak areas for each group of fragment are summed, and CrR is calculated as:

$$CrR = \frac{\text{Peak area}_{HA-X-HA}}{\text{Peak area}_{HA-X-HA} + \text{Peak area}_{HA-X}}$$

It is assumed that all types of HA-X fragments have the same response in the MS detector, i.e. a certain peak area corresponds to a given molar amount for all types of HA-X fragments (Kenne et al., Carbohydrate Polymers 91 (2013) 410-418).

When determining CrR, care should be taken to only include BDDE bound by ether linkages. Depending on the conditions during cross-linking, BDDE can bind to the HA via both ether and ester linkages. Since the ester linkages are easily hydrolyzed, it is only the ether-bound BDDE that will contribute to the gel strength and duration in the long term. The fragments with ester-bound BDDE have the same mass as the ether-bound BDDE but can be detected as they have slightly different chromatographic retention times. To determine the CrR without any ester-bound BDDE, the samples should be hydrolyzed before analysis. Hydrolysis of the samples could e.g. be made by adding base and/or heat before or after the enzymatic degradation.

Determination of pH

The pH determination is performed potentiometrically at ambient temperature using a glass electrode. The method used for pH determination of the swelled product is based on USP method <791>. Procedure: Calibrate the pH-meter at ambient room temperature with buffer solutions for standardization at pH 7.0 and 4.0. Transfer about 1.2 mL of sample (for every measurement) into a suitable container. Make sure that the sample is at room temperature. Measure the pH on duplicates of the sample. Wash the electrode in distilled water and wipe off carefully between each measurement.

The method for pH determination of the process solutions, notably the organic solvent is as above, but with calibration at pH 7.0 and 10.0.

The pH values measured in a mixture of water and organic solvent(s) differ compared to pH measured in pure water solutions for the same concentration of base, e.g. sodium hydroxide (NaOH). Therefore, the expression apparent pH ($pH_{app}$) is used for pH measured in an aqueous mixture of organic solvent(s). The apparent pH is depending on several factors, including the type of organic solvent(s), the concentration of organic solvent(s), the temperature, the ion strength and the presence of other compounds in the mixture.

The apparent pH values reported in the experimental section were measured with a Mettler Toledo MA 234 pH/Ion analyzer with a Mettler Toledo Inlab Routine Pro electrode for pH range 0-14.

Rheometry

Rhemometry in the oscillating mode is used to determine the viscoelastic properties of the swelled gel product. The elastic modulus (G') describes the gel strength in terms of the gels physical resistance to elastic deformation. The viscous modulus (G") describes the gel strength in terms of the gels physical resistance to viscous deformation. The measurement is performed using an oscillating rheometer.

Rheometry measurements are performed as follows. Frequency sweeps are made with a resting time of at least 15 minutes between sample loading and measurement, and a strain (γ) of 0.1%. A parallel plate probe with a diameter of 25 mm is used with a gap of 2 mm. Average values of the elastic modulus (G') and viscous modulus (G") are evaluated at 0.1 and 1 Hz from the frequency sweeps. Amplitude sweeps are made at 1 Hz to verify that the frequency sweep was performed at a strain (γ) within the linear viscoelastic range.

Determination of Enzyme Degradability

Enzyme degradation is performed in order to verify that the cross-linked gel is equal to native HA regarding biodegradability by confirming that it is degradable by hyaluronidase from sheep testes.

The product (dry, or swelled to a known concentration) with a predetermined weight is allowed to swell over night at 37° C. in 100 mL of 0.9% saline. Hyaluronidase from sheep testes (Type II, H2126 Sigma) is added to obtain an enzyme concentration of 200 U/mL, and the preparation is set to shake over night at 37° C. The solution is filtrated through a 0.22 μm filter, and the amount of HA in the filtrate is determined using the carbazole method. The degradation is calculated as the ratio of the amount of HA in the filtrate to the total amount of HA in the sample.

EXAMPLES

Example 1—Cross-Linking Procedures

Approximately 1 g sodium hyaluronate having a molecular weight of 0.8-3 MDa was dissolved in 10-50 mL of an aqueous solution containing 0-40% ethanol, and 0-120 mM strong base. After complete dissolution, the resulting hyaluronate solution had a $pH_{app}$ of 6-13, measured as described above. (Preparation step)

The hyaluronate solution was extruded through an opening with a 0.3-0.5 mm diameter into a liquid medium containing an organic solvent. The extruded hyaluronate solution immediately precipitated into hyaluronate fibers. (Precipitation step)

Approximately 1 g of precipitated HA fibers was then transferred to approximately 20-70 mL of an aqueous cross-linking medium containing 65-80% of an organic solvent, 0.3-1.2 g (30-230 mM) cross-linking agent, and 1-75 mM strong base. The hyaluronate remained precipitated and in the form of fibers. The resulting cross-linking medium including HA had a pH above 11.5. The HA fibers were allowed to cross-link in the aqueous/organic cross-linking medium. (Cross-linking step)

The thus obtained cross-linked hyaluronate fibers were then removed from the cross-linking medium and neutralized with phosphoric acid or the like. The cross-linked HA fibers were dried in vacuum chamber under reduced pressure (~200 mbar) at room temperature for approximately 1 hour.

The precipitated intermediate was characterised as follows. The weight of the dry cross-linked hyaluronate fibers was determined. The dried fibers were soaked in an excess of 0.9% aqueous saline and allowed to absorb liquid freely. The fibers then formed an aqueous gel, and saline was absorbed until equilibrium (maximum) swelling of the fibers was obtained. The gel fibers were removed manually from the solution of excess saline and non-cross-linked hyaluronate and transferred directly to a balance. The weight of the fully swollen fibers was determined. From the saline uptake results, a degree of swelling (SwD) was determined, corresponding to a certain sodium hyaluronate concentration in fully swelled gel ($C_{min}$).

The degree of modification (MoD) of the resulting cross-linked hyaluronate fibre was determined by NMR spectroscopy as described above. Briefly, the intensity for the signal from linked BDDE is related to the signal from the acetyl group in HA. The molar ratio of linked BDDE relative HA can then be calculated after correction for the number of protons giving rise to the signals. The corresponding modification efficiency (MoE) was calculated from the swelling degree.

The described precipitated intermediates of the cross-linked HA fibers were allowed to swell to a defined HA-concentration as follows. Phosphate buffered saline solution (4 mM phosphate and 150 mM NaCl) or the like was added to the dried HA fibers to a concentration of about 10-40 mg HA/mL. The partly swollen gel was filled into 10 mL plastic syringes. The filled syringes were sterilized using moist heat at 123° C. with a final equivalent time ($F_0$) of approximately 20 minutes. The content of the autoclaved syringes were characterised regarding pH, HA concentration, degree of swelling (SwD), and minimum concentration ($C_{min}$) with the methods described above, and MoE was calculated from the MoD determined for the intermediate.

Cross-linked HA fibers were prepared as described above. Analytical data for precipitated intermediates are reported in the Table 1, and data obtained for swelled and autoclaved products are shown in Table 2.

TABLE 1

Characterization of product (precipitated intermediate)

| Exp Id | Amount dry HA (mg) | Amount swollen HA (mg) | SwD* (g/g) | $C_{min}$ (mg/mL) | MoD (%) | MoE |
|---|---|---|---|---|---|---|
| 1 | — | — | — | — | 0.3 | — |
| 2 | 23 | 1181 | 51 | 20 | 0.7 | 28 |
| 3 | 15 | 2200 | 147 | 7 | 0.2 | 38 |
| 4 | 17 | 1070 | 62 | 16 | 0.2 | 73 |
| 5 | 17 | 1505 | 89 | 11 | 0.4 | 30 |
| 6 | 16 | 2110 | 133 | 8 | 0.2 | 42 |
| 7 | — | — | — | — | 1.3 | — |
| 8 | — | — | — | — | 0.4 | — |
| 9 | — | — | — | — | 0.5 | — |
| 10 | — | — | — | — | 0.2 | — |
| 11 | — | — | — | — | 0.3 | — |
| 12 | 16 | 501 | 32 | 31 | 1.7 | 19 |
| 13 | 15 | 313 | 21 | 48 | 0.3 | 190 |
| 14 | 19.8 | 632 | 32 | 31 | 0.7 | 46 |
| 15 | — | — | — | — | 0.5 | — |

*Measured according to procedure 1

TABLE 2

Characterization of swelled and autoclaved product

| Exp Id | pH | HA concentration (mg/mL) | SwD** (mL/g) | $C_{min}$ (mg/mL) | MoE |
|---|---|---|---|---|---|
| 1 | 6.9 | 20* | 110 | 9 | 28 |
| 2 | — | — | — | — | — |
| 3 | 7.3 | 19 | 85 | 12 | 65 |
| 4 | — | 20* | — | — | — |
| 5 | — | — | — | — | — |
| 6*** | 7.2 | 20* | 139 | 7 | 40 |
| 7 | 7.6 | 20* | 23 | 43 | 32 |
| 8 | 6.6 | 20* | 40 | 25 | 59 |
| 9 | 7.1 | 20* | 21 | 47 | 97 |
| 10 | 7.2 | 20* | 96 | 10 | 44 |
| 11 | 7.3 | 20* | 55 | 18 | 55 |
| 12 | — | — | — | — | — |
| 13 | 7.3 | 20* | 23 | 44 | 174 |
| 14 | — | — | — | — | — |
| 15 | 7.9 | 20* | 97 | 10 | 21 |

*estimated HA concentration
**measured according to procedure 3
***2 mg lidocaine hydrochloride was added per mL phosphate buffer saline solution in the swelling step described above Example 2—Cross-Linking with Different Cross-Linking Agents A hyaluronate solution was prepared as set out in Example 1 After complete dissolution, the resulting hyaluronate solution had a pH above 9, measured as described above. The hyaluronate solution was extruded through an opening with a 0.5 mm diameter into a liquid medium of 99.5% ethanol. The extruded hyaluronate solution immediately precipitated into hyaluronate fibers.

Approximately 1 g of precipitated HA fibers was transferred to an aqueous/organic cross-linking medium containing 70% ethanol, cross-linker and NaOH. The hyaluronate remained precipitated and in the form of fibers. The resulting cross-linking medium including HA, had a pH above 11.5.

The HA fibers were allowed to cross-link in the aqueous/organic cross-linking medium. The thus obtained cross-linked hyaluronate fibers were then removed from the cross-linking medium and neutralized with phosphoric acid. The cross-linked HA fibers were dried in a vacuum chamber under reduced pressure (~200 mbar) at room temperature for approximately 2 hours.

The described precipitated intermediate of the cross-linked HA fibers was allowed to swell to a defined HA concentration as follows. Phosphate buffered saline solution was added to the dried HA fibers to a concentration of about 20 mg HA/mL. The partly swollen gel was filled into 10 mL plastic syringes. The filled syringes were sterilized using moist heat at 123° C. with a final $F_0$ of approximately 20 minutes. The content of the autoclaved syringes was characterised regarding pH, degree of swelling (SwD procedure 3), minimum concentration ($C_{min}$), degree of modification (MoD) and modification efficiency (MoE), with the methods described above. The results shown in Table 3 imply that the different diepoxides are useful cross-linking agents in the described process.

TABLE 3

Characterization of product

| Cross-linker | pH | SwD* (mL/g) | $C_{min}$ (mg/mL) | MoD (%) | MoE |
|---|---|---|---|---|---|
| EDDE** | 7.6 | 24 | 41 | 1.5 | 27 |
| EDDE** | 7.3 | 12 | 86 | 2.8 | 31 |
| Diepoxyoctane | 7.9 | 97 | 10 | 0.5 | 21 |

*Measured according to procedure 3, HA conc assumed to be 20 mg/mL
**1,2-ethanediol diglycidyl ether, purity 50%

Example 3—Cross-Linking in Methanol

A hyaluronate solution was prepared as set out in Example 1. After complete dissolution, the resulting hyaluronate solution had a pH above 9, measured as described above. The hyaluronate solution was extruded through an opening with a 0.5 mm diameter into a liquid medium of 99.5% ethanol. The extruded hyaluronate solution immediately precipitated into hyaluronate fibers.

Approximately 0.75 g of precipitated HA fibers was then transferred to an aqueous cross-linking medium containing 80% methanol, 1,4-butanediol diglycidyl ether (BDDE), and NaOH. The hyaluronate remained precipitated and in the form of fibers. The resulting cross-linking medium including HA, had a pH above 11.5.

The HA fibers were allowed to cross-link in the aqueous/organic cross-linking medium. The thus obtained cross-linked hyaluronate fibers were then removed from the cross-linking medium and neutralized with phosphoric acid. The cross-linked HA fibers were dried in vacuum chamber under reduced pressure (~200 mbar) at room temperature for approximately 1 hour.

The degree of swelling was measured according to SwD procedure 1. The dried intermediate of the cross-linked fibers were allowed to swell to 20 mg HA/mL in a phosphate buffered saline solution. The swollen gel was filled into 10 mL plastic syringes. The filled syringes were sterilized using moist heat at 123° C. with a final $F_0$ of approximately 20 minutes. The content of the autoclaved syringes were characterised with respect to pH and degree of modification (MoD) according to methods described above. The resulting gel formulation had a pH of 6.8, and a MoD of 0.34%.

Example 4—Cross-Linking in Isopropanol

Hyaluronate solution was prepared as described in Example 3. Approximately 0.5 g of precipitated HA fibers was then transferred to 30 mL of an aqueous cross-linking medium containing 70% isopropanol, 1,4-butanediol diglycidyl ether (BDDE), and NaOH. The hyaluronate remained precipitated and in the form of fibers. The resulting cross-linking medium including HA, had a pH above 11.5.

The HA fibers were allowed to cross-link in the aqueous/organic cross-linking medium. The thus obtained cross-linked hyaluronate fibers were removed from the cross-linking medium and neutralized with phosphoric acid. The cross-linked HA fibers were then dried in vacuum chamber under reduced pressure (~200 mbar) at room temperature for approximately 1 hour.

The dried intermediate of the cross-linked fibers were allowed to swell in phosphate buffered saline solution to a HA-concentration of 20 mg HA/mL. The swollen gel was filled into 10 mL plastic syringes. The filled syringes were sterilized using moist heat at 123° C. with a final $F_0$ of approximately 20 minutes. The content of the autoclaved syringes were characterised with respect to pH, degree of swelling (according to procedure 3), gel content and degree of modification (MoD) according to methods described above. The minimum concentration $C_{min}$ and the modification efficiency (MoE) were calculated as described above. The resulting gel formulation had a pH of 7.6, SwD 47 g/g HA, $C_{min}$ 21 mg/mL, MoD 0.41%, and MoE 52.

Example 5—Cross-Linking in Desired Shapes and Structures

A hyaluronate solution was prepared as set out in Example 1. After complete dissolution, the resulting hyaluronate solution had a pH above 9, measured as described above.

Precipitated HA substrates with different shapes, or structures, were prepared from the above hyaluronate solution by:
1) extrusion through an opening with a diameter of 0.5 mm forming droplets;
2) extrusion through an opening with a diameter of 0.5 mm forming a net; and
3) spreading on a plastic foil forming a film,
and subsequently immersed into a liquid medium of 99.5% ethanol. The extruded hyaluronate solution immediately precipitated into hyaluronate droplets, net and film, respectively.

Approximately 1 g of each precipitated HA substrate was then transferred to 45 mL of an aqueous cross-linking medium containing 70% ethanol, 1,4-butanediol diglycidyl ether (BDDE), and NaOH. During the cross-linking reaction, the hyaluronate remained precipitated and in the predetermined forms. The resulting cross-linking medium including HA, had a pH above 11.5.

After finished cross-linking, the cross-linked hyaluronate formulations were removed manually from the cross-linking medium, neutralized with phosphoric acid and dried in vacuum chamber under reduced pressure (~200 mbar) at room temperature for approximately 1 hour before they were characterised.

The degree of swelling (SwD) was determined for the droplets and the film. A known amount of the dry cross-linked hyaluronate sample soaked in an excess of 0.9% aqueous saline and allowed to absorb liquid freely. The samples then formed aqueous gels, and saline was absorbed until equilibrium (maximum) swelling of the samples was obtained. The gel samples were then removed manually from the solution of excess saline and eventually non-cross-linked residual hyaluronate, and were transferred directly to a balance. The maximum saline uptake was estimated by comparing the weight for the swollen gels with the initial weight of the dry material. The results are presented in Table 4 both as degree of swelling (SwD procedure 1) and minimum concentration ($C_{min}$). The net was allowed to swell in an excess of 0.9% aqueous saline as described above. The swelled gel net is shown in FIG. 1.

The degree of modification (MoD) of the cross-linked hyaluronate droplets and film was determined by NMR spectroscopy as described above. Briefly, the intensity for the signal from linked BDDE is related to the signal from the acetyl group in HA. The molar ratio of linked BDDE relative HA was then calculated after correction for the number of protons giving rise to the signals. The results from MoD and the calculated modification efficiency (MoE) are presented in Table 4.

The dried intermediate of the cross-linked droplets were allowed to swell in phosphate buffered saline solution to a HA concentration of 20 mg HA/mL. The swollen gel was filled into 10 mL plastic syringes. The filled syringes were sterilized using moist heat at 123° C. with a $F_0$ of approximately 20 minutes. The results from the characterization of autoclaved droplets are also presented in Table 4.

TABLE 4

| Sample | SwD (g/g HA) | $C_{min}$ (mg/mL) | MoD (%) | MoE |
|---|---|---|---|---|
| Droplets | 60* | 17 | 0.47 | 36 |
| Autoclaved droplets | 58** | 17 | 0.47 | 37 |
| Film | 115* | 9 | 0.43 | 20 |

*measured according to procedure 1
**measured according to procedure 3

The results show that it is possible to produce cross-linked HA materials with a predefined form that is retained during the cross-linking process and autoclaving.

Example 6—Cross-Linking of Alkaline Fibers

A hyaluronate solution was prepared as set out in Example 1. After complete dissolution, the resulting hyaluronate solution had a pH above 9, measured as described above. The hyaluronate solution was extruded through a 21G needle (inner diameter 0.5 mm) into a liquid medium of 99.5% ethanol. The extruded hyaluronate solution immediately precipitated into hyaluronate fibers.

Approximately 1 g of precipitated, unwashed HA fibers was then transferred to 68 mL of an aqueous cross-linking medium containing 70% ethanol and 1,4-butanediol diglycidyl ether (BDDE). The hyaluronate remained precipitated, alkaline and in the form of fibers. The resulting cross-linking medium after addition of the alkaline HA fibers, had a pH above 11.5.

The HA fibers were allowed to cross-link in the aqueous/organic cross-linking medium. The thus obtained cross-linked hyaluronate fibers were then removed from the aqueous cross-linking medium, neutralized with phosphoric acid, dried in vacuum chamber under reduced pressure (~200 mbar) at room temperature for approximately 1 hour and characterised.

The dried intermediate of the cross-linked fibers were allowed to swell to a HA-concentration of approximately 20 mg/mL in phosphate buffered saline solution. The partly swollen gel was filled into 10 mL plastic syringes. The filled syringes were sterilized using moist heat at 123° C. with a final $F_0$ of approximately 20 minutes. The content of the autoclaved syringes were characterised with respect to pH, degree of swelling (SwD), gel content and degree of modification (MoD) according to methods described above. The minimum concentration $C_{min}$ and the modification efficiency (MoE) were calculated as described above. The results are presented in Table 5.

TABLE 5

| Formulation | pH gel formulation | SwD* (g/g HA) | $C_{min}$ (mg/mL) | MoD (%) | MoE |
|---|---|---|---|---|---|
| 1 | 6.6 | 170 | 6 | 0.10 | 59 |
| 2 | 6.8 | 51 | 20 | 0.25 | 78 |

*Measured according to procedure 3 and corrected for gel content

Thus, cross-linking of alkaline fibers in neutral cross-linking medium containing 70% alcohol with a final apparent pH above 11.5 resulted in well-defined gel fibers.

Example 7—Biocompatibility and Stability Study

Four formulations were prepared as set out in Example 1 with the purpose to study the biocompatibility of the material in vivo. After complete dissolution, the resulting hyaluronate solution had a pH above 9, measured as described above. The hyaluronate solution was extruded through an 18G (ø0.8 mm; formulations 1 and 2) or 25G (ø0.3 mm; formulations 3 and 4) wide opening into a liquid medium of 99.5% ethanol. The extruded hyaluronate solution immediately precipitated into hyaluronate fibers.

Approximately 1 g of precipitated HA fibers was then transferred to 60 mL of an aqueous cross-linking medium containing 70% ethanol, 1,4-butanediol diglycidyl ether (BDDE), and NaOH. Formulations 2 and 4 were subjected to a four times higher BDDE concentration than formulations 1 and 3. The hyaluronate remained precipitated and in the form of fibers. The resulting cross-linking medium including HA had a pH above 11.5, as measured with the equipment described above.

The HA fibers were allowed to cross-link in the aqueous/organic cross-linking medium. The thus obtained cross-linked hyaluronate fibers were then removed from the aqueous cross-linking medium, neutralized with phosphoric acid, dried in vacuum chamber under reduced pressure (~200 mbar) at room temperature for approximately 1 hour and characterised.

The dried fibers were soaked in an excess of 0.9% aqueous saline and allowed to absorb liquid freely. The fibers then formed an aqueous gel, and saline was absorbed until equilibrium (maximum) swelling of the fibers was obtained. The gel fibers were then removed manually from the solution of excess saline and non-cross-linked hyaluronate and transferred directly to a balance. The maximum saline uptake was estimated by comparing the initial weight of the precipitated material with the weight of the fully swollen fibers. The results obtained from the gel fibers before sterilization are presented in Table 6, both as degree of swelling (SwD) and minimum HA concentration ($C_{min}$).

TABLE 6

| Formulation | Weight of dry fibre (mg) | Weight of fully swollen fibre (mg) | SwD* (g/g HA) | $C_{min}$ (mg HA/mL) | MoD (%) | CrR (%) | MoE |
|---|---|---|---|---|---|---|---|
| 1 | 14 | 1144 | 81 | 12 | 0.29 | 51 | 43 |
| 2 | 26 | 739 | 28 | 36 | 1.22 | 46 | 29 |
| 3 | 14 | 1397 | 100 | 10 | 0.28 | 50 | 36 |
| 4 | 14 | 478 | 34 | 29 | 1.13 | 47 | 26 |

*Measured according to SwD procedure 1

Figure 2:
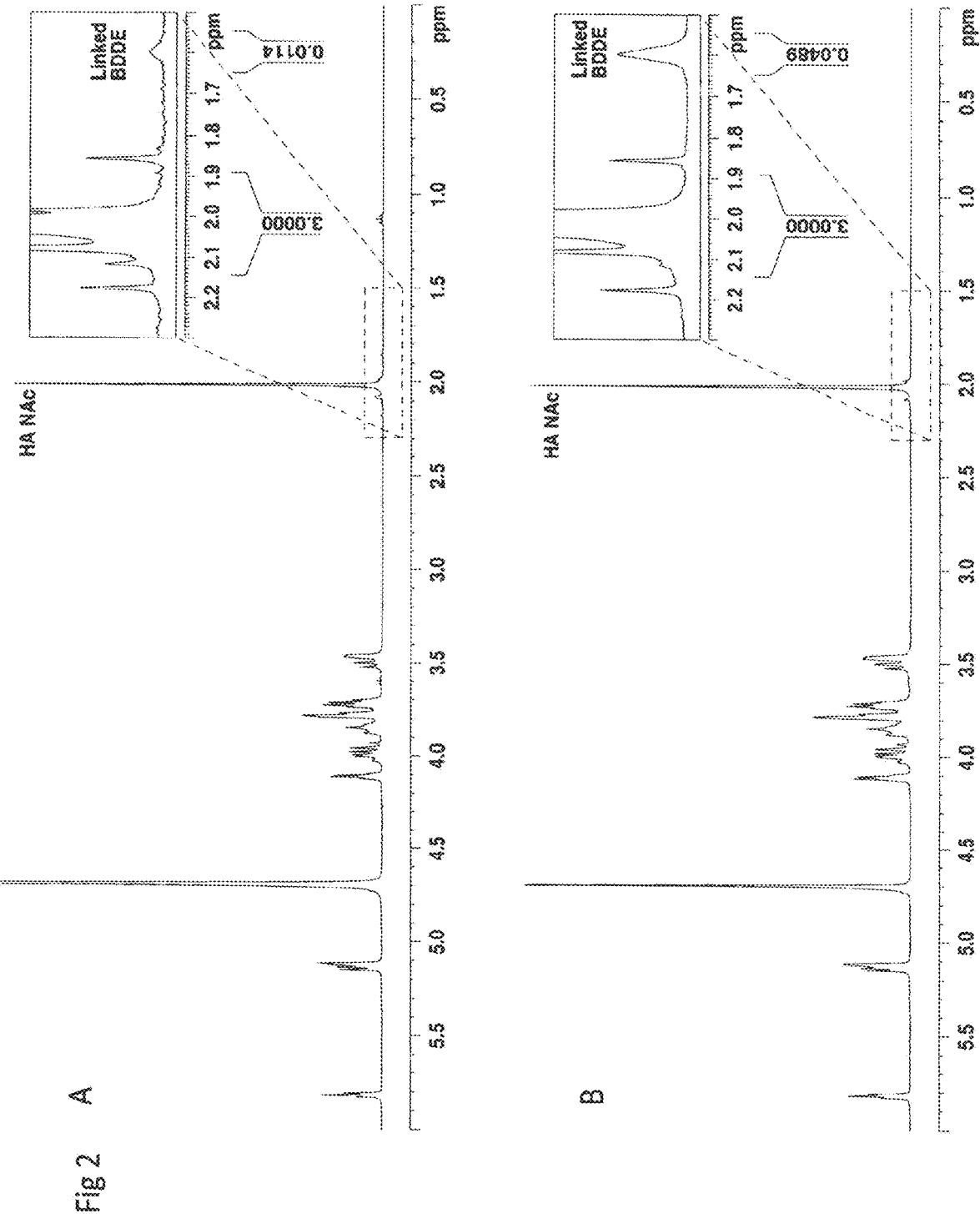
FIG. 2 shows 400 MHz $^1$H NMR spectra of two enzymatically degraded HA gel formulations.
Figure 3:
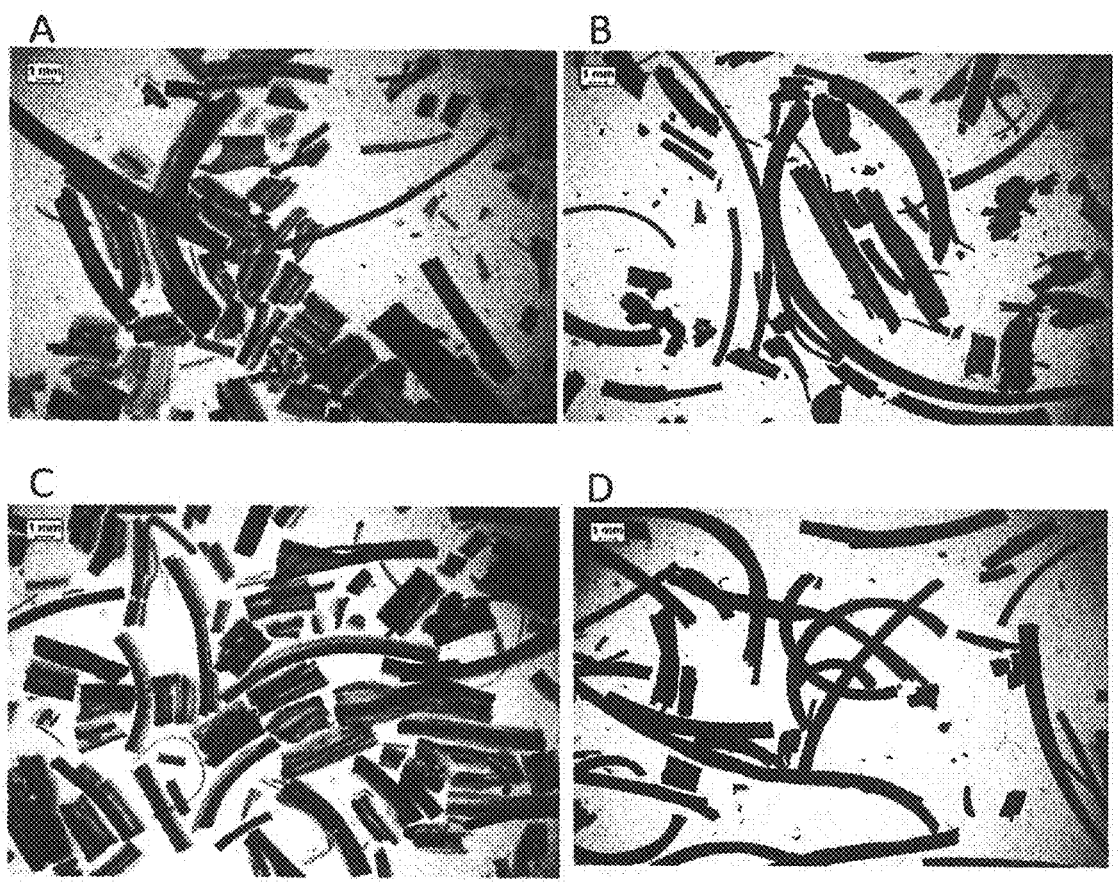
FIG. 3 shows microscopy images of cross-linked HA gel fibers.

The degree of modification (MoD) of the resulting cross-linked hyaluronate fibre was determined by NMR spectroscopy as described above. Briefly, the intensity for the signal from linked BDDE is related to the signal from the acetyl group in HA. The molar ratio of linked BDDE relative HA can then be calculated after correction for the number of protons giving rise to the signals. FIGS. 2A (formulation 1) and 2B (formulation 2) show 400 MHz $^1$H NMR spectra of enzymatically degraded HA-gel in deuterated water ($D_2O$). Signals from linked BDDE and the N-acetyl group are marked in the spectra. The result of MoD and CrR, for each respective formulation is presented in Table 6 together with the modification efficiency (MoE).

The dried intermediate of the cross-linked fibers were allowed to swell to a defined HA-concentration as follows. Phosphate buffered saline solution was added to the dried HA-fibers to achieve an estimated concentration of approximately 20 mg HA/mL. Formulation 1 and 3 absorbed all the added solution, while formulation 2 and 4 did not. The swollen gel was then filled under aseptic conditions into 1 mL glass syringes. The filled syringes were sterilized using moist heat at 125° C. with a final $F_0$ of approximately 20 minutes.

The content of the autoclaved syringes were characterised with respect to HA concentration, gel content (GelC), degree of swelling (SwD), and pH according to methods described above. The results from the product after sterilization are presented in Table 7.

TABLE 7

| Formulation | HA concentration (mg/mL) | GelC (%) | SwD* (g/g HA) | pH |
|---|---|---|---|---|
| 1 | 18 | 96 | 95 | 7.5 |
| 2 | 32 | ~99 | 25 | 7.6 |
| 3 | 19 | 95 | 87 | 7.6 |
| 4 | 36 | ~99 | 23 | 7.5 |

*Measured according to SwD procedure 3 and corrected for gel content

It is apparent from Tables 6 and 7 that formulations 1 and 3 are less rigid and less chemically modified than formulations 2 and 4. The high HA concentrations of formulations 2 and 4 reflect that the maximum uptake of water is low, and that it is not possible to achieve a gel product with lower HA concentration for a gel produced under these conditions.

The formulations were analyzed regarding bioburden (pour plate method) and endotoxins (gel-clot method). All formulations had a bioburden of 0 cfu/syringe and an endotoxin value of <0.21 EU/mL. The formulations all met the requirements regarding purity for the biocompatibility study.

Microscopy

The swelled and autoclaved fibers were visualized by coloring the fibers in a Tolouidine blue water solution for 15 minutes. The microscopy images are shown in FIG. 3A-D.

3A: Formulation 1; 3B: Formulation 2; 3C: Formulation 3; and 3D: Formulation 4. Bar=1 mm.

Stability Testing

Figure 4:
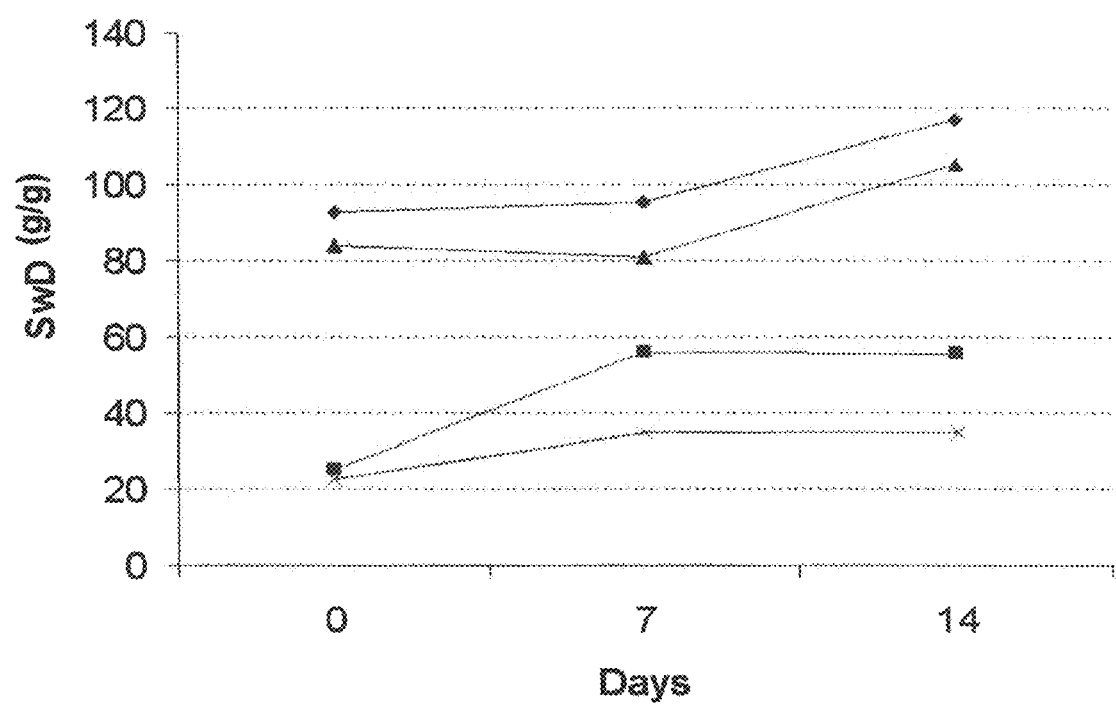
FIG. 4 is a graph showing the change in Swelling Degree (SwD) in g/g during storage at 60° C. over 14 days.

Stability testing of the formulations was performed at 60° C./ambient relative humidity (RH) for 14 days. The formulations all showed good stability. FIG. 4 shows the increase of SwD over time at 60° C. (measured according to SwD procedure 3 and corrected for gel content). Formulation 1 (♦); Formulation 2 (■); Formulation 3 (▲); and Formulation 4 (x).

Biological Evaluation

The biocompatibility of the formulations was tested by subcutaneous injections in 24 Sprague-Dawley rats. The animals were anaesthetized, shaved dorsally, and 1 mL of each formulation was injected subcutaneously. Two injections were performed on each side of the midline on the back of the rat. The animals were divided in two groups. One group was euthanized one week after injection, and the other group three weeks after injection. The animals were checked daily, and no signs of illness were recorded. The injected formulations were macroscopically and histologically well tolerated in all skin samples. Thus, no signs of necrosis or acute inflammation could be seen. No formation of granulomas or signs of tissue reaction apart from a thin fibrous capsule (not shown) that surrounded the site of the implanted formulation were found. It could be concluded that the formulations were biocompatible in rats.

Example 8—Hyaluronidase Degradation of Gels with Different Gel Strengths

A hyaluronate solution was prepared as set out in Example 1. After complete dissolution, the resulting hyaluronate solution had a pH above 11.5, measured as described above. The hyaluronate solution was extruded through an opening with a 0.5 mm diameter into a liquid medium of 99.5% ethanol. The extruded hyaluronate solution immediately precipitated into hyaluronate fibers.

Approximately 1 g of precipitated HA fibers was transferred to an aqueous/organic cross-linking medium containing 70% ethanol, BDDE and NaOH. The hyaluronate remained precipitated and in the form of fibers. The resulting cross-linking medium including HA, had a pH above 11.5.

The HA fibers were allowed to cross-link in the aqueous/organic cross-linking medium. The thus obtained cross-linked hyaluronate fibers were then removed from the cross-linking medium and neutralized with phosphoric acid. The cross-linked HA fibers were dried in a vacuum chamber under reduced pressure (~200 mbar) at room temperature for approximately 2 hours.

The described precipitated intermediate of the cross-linked HA fibers was allowed to swell to a defined HA concentration as follows. Phosphate-buffered saline solution was added to the dried HA fibers to a concentration of about 20-40 mg HA/mL. The partly swollen gel was filled into 10 mL plastic syringes. The filled syringes were sterilized using moist heat at 123° C. with a final $F_0$ of approximately 20 minutes. The content of the autoclaved syringes was characterised regarding degree of swelling (SwD procedure 2), HA concentration, minimum HA concentration ($C_{min}$), degree of modification (MoD), modification efficiency (MoE), and viscoelastic properties according to the methods described above. All the different products were subjected to hyaluronidase degradation according to "Determination of enzyme degradability" to verify that the biodegradability of HA is maintained in the cross-linked product.

The results are reported in Tables 8A and 8B. The values of G'/(G'+G") are >70% for all formulations which clearly shows that they all are gels. Furthermore, the G' values show that the gels are firm. Nevertheless, the gels are degradable by hyaluronidase to more than 99% over a large span of gel strength, as shown by the determined swelling properties and rheological properties. This shows that the biodegradability of the native HA advantageously is maintained in the gel products according to the invention.

TABLE 8A

| | Cross-linking process | Characterization | | | | |
|---|---|---|---|---|---|---|
| | | | | | Degradation | |
| Sample | Conc. cross-linker | SwD* (mL/g) | $C_{min}$ (mg/mL) | MoD (%) | by hyaluronidase (%) | HA conc (mg/mL) |
| 1 | 1× | 75 | 14 | 0.2 | >99 | 20 |
| 2 | 2× | 26 | 39 | 0.4 | >99 | 17 |
| 3** | 6× | 17 | 59 | 1.9 | >99 | 44 |
| 4 | 8× | 17 | 59 | 1.6 | >99 | 39 |

*Measured according to procedure 2
**Cross-linking temperature 29° C.

TABLE 8B

| Sample | G' 1 Hz (Pa) | G" 1 Hz (Pa) | G' 0.1 Hz (Pa) | G" 0.1 Hz (Pa) | G' 1 Hz (%)* | G' 0.1 Hz (%)* |
|---|---|---|---|---|---|---|
| 1 | 202 | 90 | 117 | 47 | 69% | 71% |
| 2 | 435 | 45 | 674 | 36 | 91% | 95% |
| 3 | 7975 | 527 | 7207 | 689 | 94% | 91% |
| 4 | 6485 | 352 | 5914 | 478 | 95% | 93% |

*Gel characteristic calculated as G'/(G' + G").

Example 9—Comparative Example

Five hyaluronic acid (HA) gel samples were prepared according to Example 4 in EP 2 199 308 A1, see Table 9A below. A reference sample according to the invention (FU0509:1) was prepared using the cross-linking procedure set out in Example 1 hereinabove.

TABLE 9A

| | | Cross-linking conditions | | |
|---|---|---|---|---|
| Sample | HA supplier | Stirring during cross-linking | Temperature during cross-linking | Reaction time (h) |
| 1 | Shiseido | No | RT | 16 h |
| 2 | Shiseido | Magnet | RT | 16 h |
| 3 | Shiseido | No | 45° C. | 16 h |
| 4 | Shiseido | Magnet | 40° C. | 16 h |
| 5 | Food Chemifa | Propeller | RT | 16 h |
| Reference sample | Food Chemifa | N/A | RT | 48 h |

TABLE 9B

| | Results | | | | |
|---|---|---|---|---|---|
| Sample | MoD (%) | G' 0.1 Hz | G" 0.1 Hz | G' 1 Hz | G" 1 Hz |
| 1 | 0.34 | 57 | 50 | 174 | 110 |
| 2 | 0.53 | 58 | 37 | 141 | 80 |
| 3 | 1.05 | 78 | 24 | 127 | 48 |

TABLE 9B-continued

| | | Results | | | |
|---|---|---|---|---|---|
| Sample | MoD (%) | G' 0.1 Hz | G" 0.1 Hz | G' 1 Hz | G" 1 Hz |
| 4 | 0.79 | 32 | 13 | 58 | 28 |
| 5 | 1.70 | 145 | 6 | 157 | 10 |
| Reference sample | 0.36 | 853 | 40 | 932 | 53 |

Gels were achieved for all samples, see Table 9B. The irregularly shaped gel particles provided by comparative samples 1-5 displayed MoD values in the same range as the sample prepared by the method according to the invention. However, the G' and G" values are significantly lower for the comparative samples 1-5 compared to the sample prepared by the method according to the invention. It is concluded that the method according to the invention is more efficient than the method disclosed in EP 2 199 308 A1, since the present invention provides stronger gels already at a lower MoD.

Figure 5:
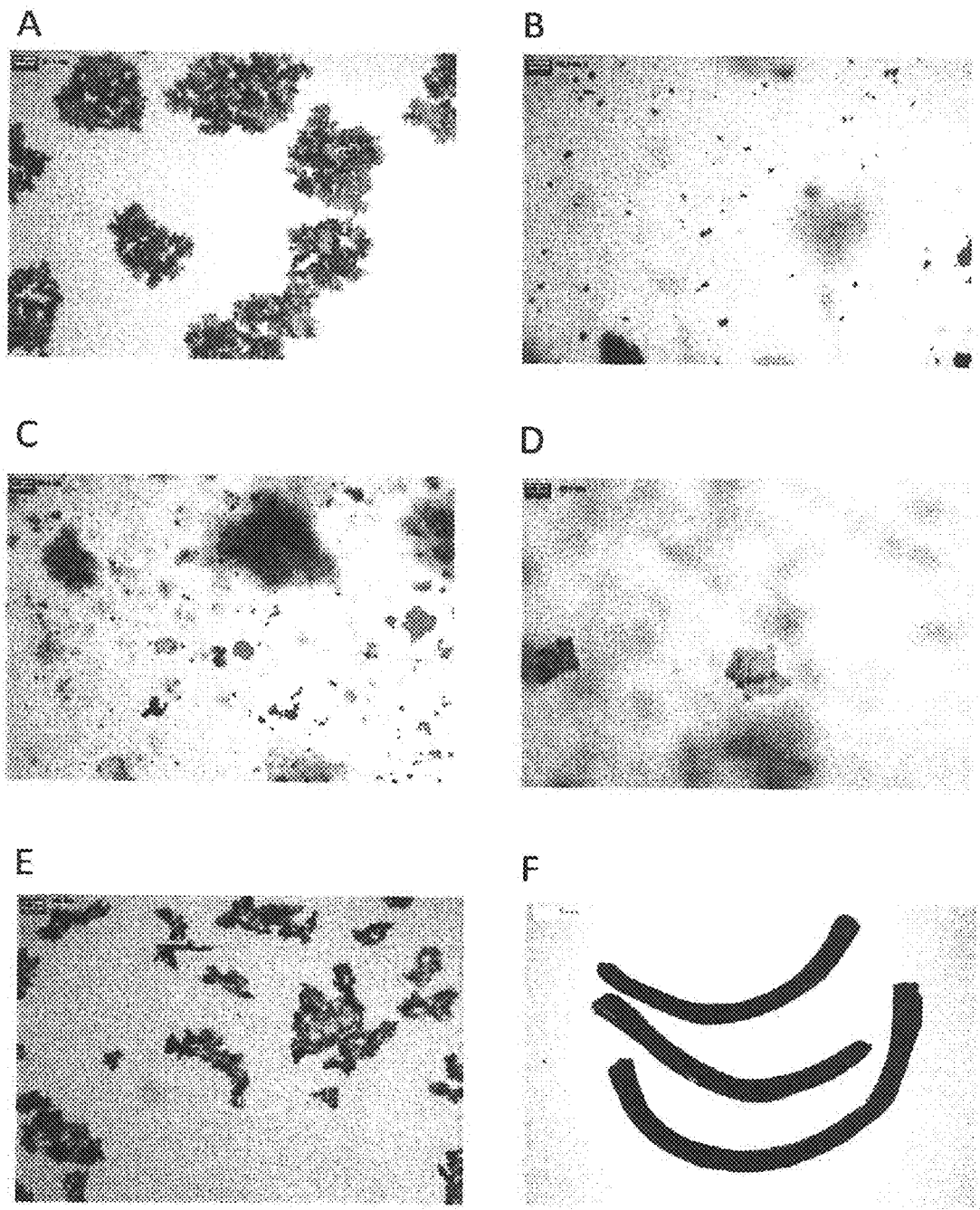
FIG. 5 shows microscopy images of a cross-linked HA powder (comparative example) and a product according to the invention.

The microscopy images of comparative samples 1-5 (FIG. 5A-E, respectively, each with 50× magnification) show a wide distribution in product size and shape, indicating that the method disclosed in EP 2 199 308 A1 provides randomly sized particles. The shape and size of the resulting particles are not under control. In contrast, the microscopy image of the product prepared by the method according to the invention (FIG. 5F) shows a product with a uniform size and shape.

Example 10—Ethanol Concentrations in the Precipitation Step

The effect of precipitating HA strings in different ethanol concentrations was tested. Four aqueous ethanol solutions with concentrations 65, 75, 85, 95% w/w were prepared. A solution of HA (5% w/w) in ethanol (35% w/w) with 0.5% NaOH (w/w) was extruded manually on small plastic (PE) films, which were immersed in baths with each of the ethanol solutions and pure (99.5% w/w) ethanol, or stepwise immersed for one min in 75% and 85% ethanol and then transferred to 99.5% ethanol.

The resulting precipitated strings were collected and visually evaluated using light microscopy. The sensory feeling when handling the strings was also evaluated. The strings were observed to have a smoother and more even surface and be more curled, more brittle and showed more bundle structure the higher the ethanol concentration had been in the precipitation bath.

Strings that were stepwise precipitated (75%→85%→99.5%) behaved like the strings that were only precipitated in 75 w/w % or 85 w/w %. No complete precipitation of the HA was observed with 65% ethanol under these conditions. A sample that was kept in 65% ethanol for 20 min and thereafter fully precipitated in 99.5% ethanol had a completely different appearance than the other strings; flat and thin band-like without bundle structures.

Example 11—Arranging a Desired Shape on a Hydrophobic Surface

The effect of the precipitation approach was tested by comparing the two following procedures:
(I): 1) extrusion—2) placed on a PE film—3) precipitation in 99.5% ethanol (c.f. Example 10)
(II): 1) extrusion—2) free falling through 99.5% ethanol—3) landing on a PE film The resulting precipitated strings were collected and visually evaluated using light microscopy. The sensory feeling when handling the strings was also evaluated. It was concluded that in the first type of precipitation procedure (I), smooth and even strings were achieved, while in the second type of precipitation procedure (II), brittle and uneven strings with bumps were obtained.

Example 12—Subcutaneous Injection in Rats

Figure 6:
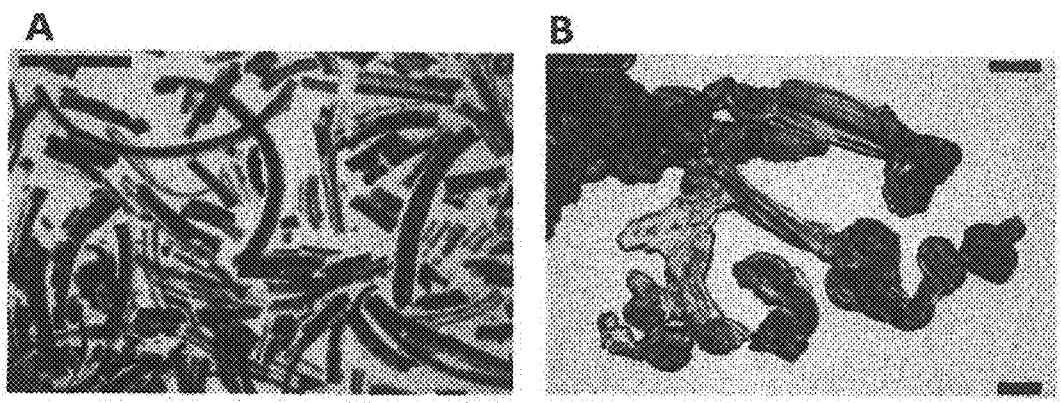
FIG. 6 shows microscopy images of cross-linked HA gel fibers.

A gel formulation prepared in essentially the same way as described in Example 7 was tested in vivo by subcutaneous injection in hairless rats (Sprague Dawley). It was observed that the string shape of the implanted gel (FIG. 6A) remains after 6 months (FIG. 6B) in the subcutaneous area in the rat. FIG. 6A shows strings (non explant) diluted in Milli-RX and colored with Toluidine blue after extrusion through an 18G cannula. FIG. 6B shows the same string batch explanted from subcutaneous area in rat after 6 months.

It is concluded that the string shape is retained after extrusion through a needle as well as after 6 months in rat.

Example 13—Comparative Example

US 2012/0034462 A1 suggests without experimental evidence that thin strands of a cross-linked HA gel can be produced by passing a solid mass of the cross-linked HA gel through a sieve or mesh. To test this theory, a gel was prepared according to Example 1 of US 2012/0034462 A1 (HA MW 3 MDa; BDDE 75 mg/g HA; temperature 50° C. for 2 hours). The hydrogel was passed through a 32 µm or 63 µm mesh screen once.

Figure 7:
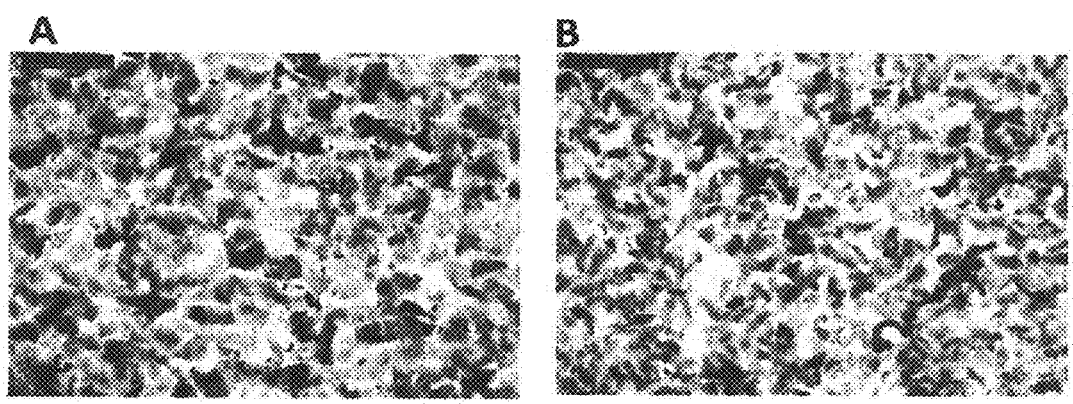
FIG. 7 shows microscopy images of a cross-linked HA gel passed once through mesh screens (comparative example).

The resulting HA gel structures in 10× amplification are shown in FIG. 7, (A) 32 µm mesh size; (B) 63 µm mesh size (bar=2 mm). The resulting particles did not display any ordered structure, and in particular not any elongated shape.

Embodiments

1. Method for manufacturing a shaped cross-linked hyaluronic acid product, comprising the steps of:
(i) providing a hyaluronic acid substrate dissolved in a first liquid medium, which is an aqueous solution, without any cross-linking;
(ii) precipitating the hyaluronic acid substrate by subjecting it to a second liquid medium comprising an amount of one or more first water-soluble organic solvent(s) giving precipitating conditions for hyaluronic acid without any cross-linking; wherein step (i) and/or step (ii) further comprises arranging the hyaluronic acid substrate in a desired shape; and
(iii) subjecting the non-cross-linked precipitated hyaluronic acid substrate in the desired shape to a single cross-linking reaction in a third liquid medium having a pH of 11.5 or higher and comprising one or more polyfunctional cross-linking agent(s) and an amount of one or more second organic solvent(s) giving precipitating conditions for hyaluronic acid, under suitable conditions to obtain a precipitated, shaped cross-linked hyaluronic acid product.
2. Method according to embodiment 1, wherein the first two steps (i) and (ii) occur in the absence of a cross-linking agent, and wherein the polyfunctional cross-linking agent(s) is added in the third cross-linking step (iii).
3. Method according to any preceding embodiment, wherein step (i) further comprises arranging the hyaluronic acid substrate solution in a desired shape on a hydrophobic surface; and wherein the precipitation of the shaped hyaluronic acid substrate in step (ii) occurs on said hydrophobic surface.

4. Method according to embodiment 3, wherein said hydrophobic surface is selected from fluorocarbons, polypropylene (PP), polyethylene terephthalate glycol-modified (PETG), polyethylene (PE), and polytetrafluoroethylene (PTFE).

5. Method according to any preceding embodiment, wherein said shape is selected from the group consisting of a particle, a fibre, a string, a strand, a net, a film, a disc and a bead.

6. Method according to embodiment 5, wherein said shape is a fibre and the ratio between its length and its width is 10:1 or higher.

7. Method according to any one of embodiments 1-2, wherein step (ii) involves extruding the hyaluronic acid substrate into the second liquid medium comprising an amount of the first water-soluble organic solvent(s) giving precipitating conditions for hyaluronic acid, thereby allowing the extruded hyaluronic acid substrate to form a precipitated fibre in the second liquid medium.

8. Method according to any preceding embodiment, wherein the second liquid medium of step (ii) contains 0-30 vol % water and 70-100 vol % of the first water-soluble organic solvent(s).

9. Method according to embodiment 8, wherein the second liquid medium of step (ii) contains 0-10 vol % water and 90-100 vol % of the first water-soluble organic solvent(s).

10. Method according to any preceding embodiment, wherein the third liquid medium of step (iii) contains 0-35 vol % water, 65-100 vol % of the second organic solvent(s), and one or more polyfunctional cross-linking agent(s).

11. Method according to any preceding embodiment, wherein the organic solvent(s) is individually selected from one or more lower alkyl alcohol(s).

12. Method according to any preceding embodiment, wherein the aqueous solution of step (i) contains 40-100 vol % water and 0-60 vol % of lower alkyl alcohol(s).

13. Method according to any one of embodiments 11-12, wherein the lower alkyl alcohol is ethanol.

14. Method according to any preceding embodiment, said polyfunctional cross-linking agent(s) being individually selected from the group consisting of divinyl sulfone, multiepoxides and diepoxides.

15. Method according to embodiment 14, said polyfunctional cross-linking agent(s) being individually selected from the group consisting of 1,4-butanediol diglycidyl ether (BDDE), 1,2-ethanediol diglycidyl ether (EDDE) and diepoxyoctane.

16. Method according to embodiment 15, wherein said polyfunctional cross-linking agent is 1,4-butanediol diglycidyl ether (BDDE).

17. Method according to any preceding embodiment, further comprising the steps of:
(iv) subjecting the precipitated cross-linked hyaluronic acid product to non-precipitating conditions; and
(v) isolating the cross-linked hyaluronic acid product in non-precipitated form.

18. Method according to embodiment 17, wherein step (v) further comprises sterilizing the cross-linked hyaluronic acid product.

19. A shaped cross-linked hyaluronic acid product having a degree of modification of 1-40 cross-linking agent units per 1000 disaccharide units, a swelling degree of 4-300 mL per g hyaluronic acid, and a modification efficiency of 10 or higher.

20. A shaped cross-linked hyaluronic acid product according to embodiment 19, wherein the product has a shape selected from the group consisting of a particle, a fibre, a string, a strand, a net, a film, a disc and a bead.

21. A shaped cross-linked hyaluronic acid product according to embodiment 20, wherein the product is a fibre and the ratio between its length and its width is 10:1 or higher.

22. A shaped cross-linked hyaluronic acid product according to any one of embodiments 20-21, wherein the product is a fibre, and wherein its longitudinal extension is more than 2 mm.

23. A shaped cross-linked hyaluronic acid product according to any one of embodiments 19-22, wherein said swelling degree is 15-180 mL per g hyaluronic acid.

24. A shaped cross-linked hyaluronic acid product according to any one of embodiments 19-23, wherein the modification efficiency is in the range of 20-190.

25. A shaped cross-linked hyaluronic acid product according to any one of embodiments 19-24, wherein the cross-linker ratio is 35% or higher.

26. A shaped cross-linked hyaluronic acid product according to any one of embodiments 19-25, which is cross-linked with one or more polyfunctional cross-linking agent(s) individually selected from the group consisting of divinyl sulfone, multiepoxides and diepoxides.

27. A shaped cross-linked hyaluronic acid product according to embodiment 26, said polyfunctional cross-linking agent(s) being individually selected from the group consisting of 1,4-butanediol diglycidyl ether (BDDE), 1,2-ethanediol diglycidyl ether (EDDE) and diepoxyoctane.

28. A shaped cross-linked hyaluronic acid product according to embodiment 27, wherein the polyfunctional cross-linking agent is 1,4-butanediol diglycidyl ether (BDDE).

29. A shaped cross-linked hyaluronic acid product according to any one of embodiments 19-28, wherein the product is sterilized.

30. A shaped cross-linked hyaluronic acid product manufactured by the method of any one of embodiments 1-18.

31. An aqueous composition comprising a shaped cross-linked hyaluronic acid product according to any one of embodiments 19-30, and optionally a buffering agent.

32. Use of a shaped cross-linked hyaluronic acid product according to any one of embodiments 19-30 or an aqueous composition according to embodiment 31 in cosmetic surgery.

33. Use according to embodiment 32 in cosmetic surgery selected from dermal filling and body contouring.

34. A shaped cross-linked hyaluronic acid product according to any one of embodiments 19-30 or an aqueous composition according to embodiment 31 for use as a medicament or medical device.

35. A shaped cross-linked hyaluronic acid product according to any one of embodiments 19-30 or an aqueous composition according to embodiment 31 for use in cosmetic or medical surgery.

36. A shaped cross-linked hyaluronic acid product or an aqueous composition for use according to embodiment 35 in cosmetic surgery selected from dermal filling and body contouring.

37. A shaped cross-linked hyaluronic acid product or an aqueous composition for use according to embodiment 35 in medical surgery selected from dermal filling, body contouring, prevention of tissue adhesion, formation of channels, incontinence treatment, and orthopaedic applications.

38. A shaped cross-linked hyaluronic acid product according to any one of embodiments 19-30 or an aqueous composition according to embodiment 31 for use in drug delivery.

39. A pre-filled syringe, which is pre-filled with a sterilized, shaped cross-linked hyaluronic acid product according to any one of embodiments 19-30 or a sterilized aqueous composition according to embodiment 31.

40. A method of treatment of a subject undergoing cosmetic or medical surgery, involving administration of a shaped cross-linked hyaluronic acid product according to any one of embodiments 19-30 or an aqueous composition according to embodiment 31 to a subject in need thereof.

The invention claimed is:

1. A string product with a length to width ratio of at least 10:1, comprising multiple layers of hyaluronic acid (HA) and an external layer of cross-linked HA.

2. The product according to claim 1, wherein the string comprises an internal layer of non-cross-linked HA.

3. The product according to claim 1, wherein the string comprises an internal layer of cross-linked HA that exhibits a different degree of modification than the external layer.

4. The product according to claim 3, wherein the internal layer of cross-linked HA exhibits a lower degree of modification than the external layer.

5. The product according to claim 1, wherein one or more of the multiple layers is formed by extrusion.

6. The product according to claim 1, wherein the string has a length to width ratio of at least 100:1.

7. The product according to claim 1, wherein the string has a length to width ratio of at least 25000:1.

8. The product according to claim 1, wherein the string has a diameter less than 1 mm.

9. The product according to claim 1, wherein the string has a diameter from 0.3 to 0.5 mm.

10. The product according to claim 1, wherein the string has a diameter from 0.5 to 1 mm.

11. The product according to claim 1, wherein the HA is of non-animal origin.

12. The product according to claim 1, wherein the string is woven together to form a net.

13. The product according to claim 12, wherein the net is greater than 5 mm in at least one dimension.

14. The product according to claim 1, wherein the string is dry.

15. The product according to claim 1, wherein the string is partially swollen.

16. The product according to claim 1, further comprising one or more drugs.

17. The product according to claim 16, wherein the one or more drugs are selected from the group consisting of: an anesthetic, an anti-inflammatory agent, an antibiotic, and a growth factor.

18. The product according to claim 1, further comprising one or more proteins.

19. The product according to claim 1, further comprising one or more cells.

20. The product according to claim 19, wherein the one or more cells are human cells.

21. A composition comprising a string product with a length to width ratio of at least 10:1, comprising multiple layers of hyaluronic acid (HA) and an external layer of cross-linked HA.

22. The composition according to claim 21, wherein the composition is sterile.

23. The composition according to claim 21, further comprising a buffering agent.

24. A composition comprising a plurality of string products with a length to width ratio of at least 10:1, wherein the string products comprise multiple layers of hyaluronic acid (HA) and an external layer of cross-linked HA.

25. The composition according to claim 24, wherein at least 50% of the string products have a length to width ratio of at least 20:1.

* * * * *